(12) United States Patent
Walter et al.

(10) Patent No.: US 10,519,475 B1
(45) Date of Patent: Dec. 31, 2019

(54) BIOSYNTHESIS OF COMPOUNDS IN YEAST

(71) Applicant: Amyris, Inc., Emeryville, CA (US)

(72) Inventors: Jessica Walter, Albany, CA (US); Joshua A. Lerman, Emeryville, CA (US); Michael Leavell, Emeryville, CA (US); Benjamin Yap, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 0 days.

(21) Appl. No.: 16/198,545

(22) Filed: Nov. 21, 2018

(51) Int. Cl.
| | | |
|---|---|---|
| *C12P 19/12* | (2006.01) | |
| *C12N 15/81* | (2006.01) | |
| *C07H 13/04* | (2006.01) | |
| *C12N 9/10* | (2006.01) | |
| *C12N 9/24* | (2006.01) | |
| *C12N 9/12* | (2006.01) | |
| *C12N 9/88* | (2006.01) | |

(52) U.S. Cl.
CPC .............. C12P 19/12 (2013.01); C07H 13/04 (2013.01); C12N 9/1059 (2013.01); C12N 9/1081 (2013.01); C12N 9/1205 (2013.01); C12N 9/1241 (2013.01); C12N 9/2402 (2013.01); C12N 9/88 (2013.01); C12N 15/81 (2013.01); *C12Y 204/01029* (2013.01); *C12Y 204/01069* (2013.01); *C12Y 204/01086* (2013.01); *C12Y 204/01146* (2013.01); *C12Y 204/99001* (2013.01); *C12Y 207/07023* (2013.01); *C12Y 207/07038* (2013.01); *C12Y 207/07043* (2013.01); *C12Y 302/01023* (2013.01); *C12Y 302/01038* (2013.01); *C12Y 302/01183* (2015.07); *C12Y 402/01047* (2013.01)

(58) Field of Classification Search
None
See application file for complete search history.

(56) References Cited

U.S. PATENT DOCUMENTS

| | | | |
|---|---|---|---|
| 2015/0133647 A1* | 5/2015 | Peltier-Pain | C12P 19/44 536/17.9 |
| 2016/0186223 A1* | 6/2016 | Jennewein | C12P 19/14 435/100 |

* cited by examiner

*Primary Examiner* — Anand U Desai
(74) *Attorney, Agent, or Firm* — Kilpatrick Townsend & Stockton LLP

(57) ABSTRACT

Provided herein are genetically modified yeast cells capable of producing one or more human milk oligosaccharides. The yeast cells include one or more heterologous nucleic acids that encode enzymes of a human milk oligosaccharide biosynthetic pathway. The yeast cells do not include a heterologous nucleic acid encoding a fucokinase. Also provided are fermentation compositions including the disclosed genetically modified yeast cells, and related methods of producing and recovering human milk oligosaccharides generated by the yeast cells.

28 Claims, 9 Drawing Sheets

BIOSYNTHESIS OF COMPOUNDS IN YEAST

BACKGROUND

Human milk oligosaccharides (HMOs) are the third most abundant component of human milk, with only lactose and lipids present in higher concentrations. The category of HMOs is quite diverse, with more than 200 different species so far identified in human milk. There is growing evidence attributing various health benefits to these milk compounds. Exemplary benefits include the promotion of the growth of protective intestinal microbes such as bifidobacteria, an increase in protection from gastrointestinal infections, a strengthening of the immune system, and an improvement in cognitive development. Because HMOs are not found in other milk sources, e.g., cow or goat, the only source of HMOs has traditionally been mother's milk. In an effort to improve the nutritional value of infant formula, as well as to explore the use of HMOs as child and adult nutrition, there is therefore an increased interest in the synthetic production of these compounds. The current disclosure addresses this and other needs.

BRIEF SUMMARY

In one aspect the disclosure relates to a genetically modified yeast cell capable of producing one or more human milk oligosaccharides. The yeast cell comprises one or more heterologous nucleic acids, wherein each nucleic acid independently encodes at least one enzyme of a human milk oligosaccharide biosynthetic pathway. The yeast cell does not comprise a heterologous nucleic acid encoding a fucokinase. In some embodiments, the one or more heterologous nucleic acids are integrated into the genome of the yeast cell.

In some embodiments, the one or more human milk oligosaccharides comprise 2'-fucosyllactose. In some embodiments, the enzymes encoded by the one or more heterologous nucleic acids comprise one or more of a GDP-mannose 4,6-dehydratase, a GDP-L-fucose synthase, an α-1,2-fucosyltransferase, and an α1-3,4-fucosidase.

In some embodiments, the one or more human milk oligosaccharides comprise 3-fucosyllactose. In some embodiments, the enzymes encoded by the one or more heterologous nucleic acids comprise one or more of a GDP-mannose 4,6-dehydratase, a GDP-L-fucose synthase, an α-1,3-fucosyltransferase, and an α1-3,4-fucosidase.

In some embodiments, the one or more human milk oligosaccharides comprise lacto-N-tetraose. In some embodiments, the enzymes encoded by the one or more heterologous nucleic acids comprise one or more of a β-1,3-N-acetylglucosaminyltransferase, a β-1,3-galactosyltransferase, and a UDP-N-acetylglucosamine diphosphorylase.

In some embodiments, the one or more human milk oligosaccharides comprise lacto-N-neotetraose. In some embodiments, the enzymes encoded by the one or more heterologous nucleic acids comprise one or more of a β-1,3-N-acetylglucosaminyltransferase, a β-1,4-galactosyltransferase, and a UDP-N-acetylglucosamine diphosphorylase.

In some embodiments, the one or more human milk oligosaccharides comprise 3'-sialyllactose. In some embodiments, the enzymes encoded by the one or more heterologous nucleic acids comprise one or more of a CMP-Neu5Ac synthetase, a sialic acid synthase, a UDP-N-acetylglucosamine 2-epimerase, a UDP-N-acetylglucosamine diphosphorylase, and a CMP-N-acetylneuraminate-β-galactosamide-α-2,3-sialyltransferase.

In some embodiments, the one or more human milk oligosaccharides comprise 6'-sialyllactose. In some embodiments, the enzymes encoded by the one or more heterologous nucleic acids comprise one or more of a CMP-Neu5Ac synthetase, a sialic acid synthase, a UDP-N-acetylglucosamine 2-epimerase, a UDP-N-acetylglucosamine diphosphorylase, and a β-galactoside-α-2,6-sialyltransferase.

In some embodiments, the one or more human milk oligosaccharides comprise difucosyllactose. In some embodiments, the enzymes encoded by the one or more heterologous nucleic acids comprise one or more of a GDP-mannose 4,6-dehydratase, a GDP-L-fucose synthase, an α-1,2-fucosyltransferase, and an α-1,3-fucosyltransferase.

In some embodiments, the yeast cell is *Saccharomyces cerevisiae*, and the enzymes encoded by the one or more heterologous nucleic acids further comprise a lactose permease. In some embodiments, the yeast cell is *Kluyveromyces marxianus*, wherein the yeast cell further comprises a deletion of at least a portion of a nucleic acid encoding β-galactosidase, or a decreased expression of β-galactosidase relative to that of wild-type *Kluyveromyces marxianus*.

In some embodiments, expression of at least one of the one or more heterologous nucleic acids is negatively regulated by the activity of a promoter that is responsive to a small molecule. In some embodiments, the small molecule is maltose or lysine.

In another aspect, the disclosure relates to a method of producing one or more human milk oligosaccharides. The method comprises providing a population of genetically modified yeast cells capable of producing one or more human milk oligosaccharides. Each yeast cell comprises one or more heterologous nucleic acids, and each nucleic acid independently encodes an enzyme of a human milk oligosaccharide biosynthetic pathway. The method further comprises providing a culture medium comprising sucrose and lactose, wherein the mass ratio of the sucrose to the lactose is less than 40. The method further comprises culturing the yeast cells in the culture medium under conditions suitable for the yeast cells to produce the one or more human milk oligosaccharides.

In some embodiments, the method further comprises, prior to the culturing, growing the population of genetically modified yeast cells in a growth medium comprising a small molecule, wherein expression of at least one of the one or more nucleic acids is negatively regulated by the activity of a promoter responsive to the small molecule, and wherein the concentration of the small molecule in the culture medium during the culturing is sufficiently low that the promoter is no longer active. In some embodiments, the small molecule is maltose or lysine.

In some embodiments, the population of genetically modified yeast cells comprises any of the genetically modified yeast cells disclosed herein. In some embodiments, the one or more human milk oligosaccharides comprise 2'-fucosyllactose, and the yield of the 2'-fucosyllactose on the sucrose is greater than 0.01 g/g. In some embodiments, the concentration of the 2'-fucosyllactose in the culture medium is greater than 5 g/l. In some embodiments, the yeast cells produce less than 1 g difucosyllactose per g of the produced 2'-fucosyllactose. In some embodiments, the culture medium does not comprise fucose. In some embodiments, the method further comprises adjusting the mass ratio of the sucrose to the lactose, thereby altering the production of at least one of the one or more human milk oligosaccharides.

In another aspect, the disclosure relates to a fermentation composition. The fermentation composition comprises a population of genetically modified yeast cells comprising any of the genetically modified yeast cells as disclosed herein. The fermentation composition further comprises a culture medium comprising one or more human milk oligosaccharides produced from the yeast cells.

In some embodiments, the culture medium further comprises sucrose and lactose, and the mass ratio of the sucrose to the lactose is less than 40. In some embodiments, the molar fraction of the one or more human milk oligosaccharides comprising difucosyllactose is less than 50%. In some embodiments, the molar fraction of the one or more human milk oligosaccharides comprising difucosyllactose is greater than or equal to 50%. In some embodiments, the culture medium does not comprise fucose.

In another aspect, the disclosure relates to a method of recovering one or more human milk oligosaccharides from any of the fermentation compositions disclosed herein. The method comprises separating at least a portion of the population of genetically modified yeast cells from the culture medium. The method further comprises contacting the separated yeast cells with a heated aqueous wash liquid. The method further comprises removing the wash liquid from the separated yeast cells.

In some embodiments, the heated aqueous wash liquid has a temperature greater than 48° C. In some embodiments, one or both of the separating and removing comprises centrifugation. In some embodiments, the culture medium and the wash liquid together comprise at least 70% by mass of at least one of the one or more human milk oligosaccharides produced from the yeast cells.

In another aspect, the disclosure relates to a method of treating a fermentation composition. The method includes providing a fermentation composition comprising difucosyllactose. The method further comprises contacting the fermentation composition with α1-3,4 fucosidase under conditions suitable for catalyzing the conversion of at least a portion of the difucosyllactose to 2'-fucosyllactose with the α1-3,4 fucosidase.

In some embodiments, at least 50 mol % of the difucosyllactose is converted by the α1-3,4 fucosidase. In some embodiments, the fermentation composition is any of the fermentation compositions disclosed herein.

DETAILED DESCRIPTION

I. General

Provided herein are compositions and methods useful for the production of one or more human milk oligosaccharides from genetically modified yeast cells. Human milk oligosaccharides are unconjugated complex carbohydrates having a common disaccharide lactose core. The wide variety of human milk oligosaccharide compounds are further elaborated by the addition of monosaccharides in various linkages and stereochemistries to this lactose. Monosaccharides found in human milk oligosaccharides include fucose (Fuc), galactose (Gal), N-acetyl-glucosamine (GlcNAc), and N-Acetyl neuraminic acid (Neu5Ac, commonly called sialic acid).

Figure 1:
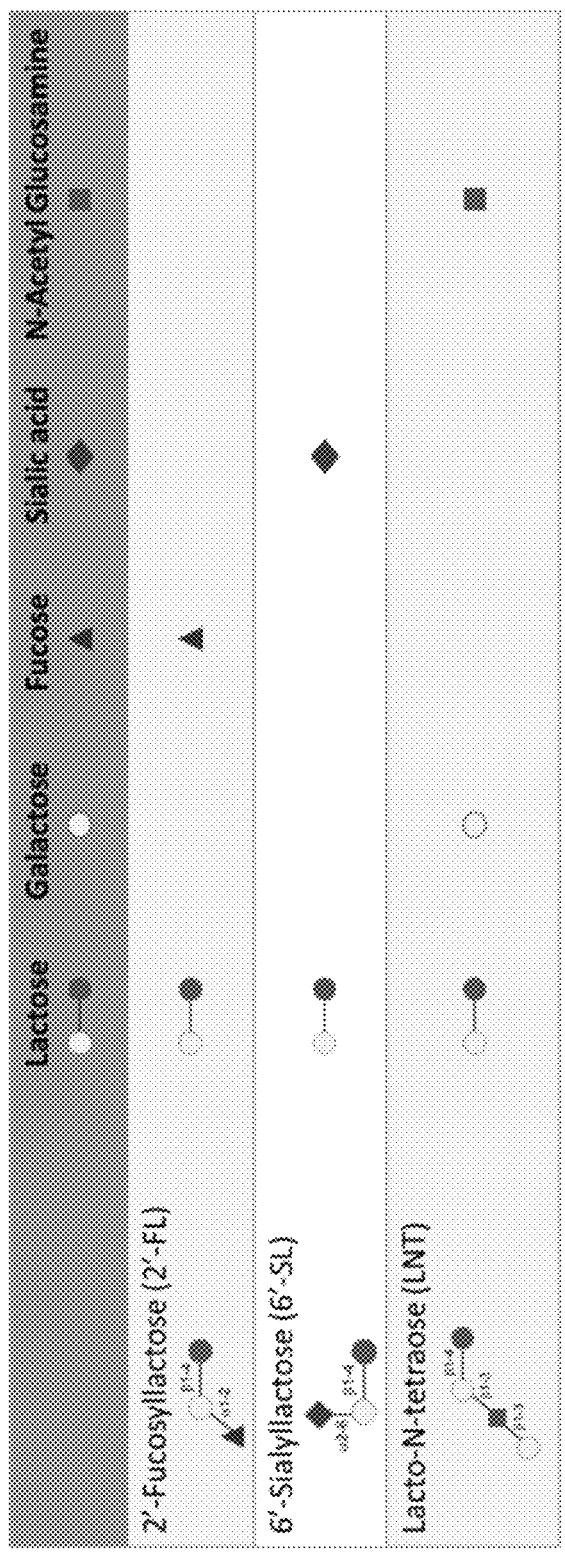
FIG. 1 presents schematic examples of human milk oligosaccharides formed from activated sugars.

FIG. 1 schematically illustrates the structures of three human milk oligosaccharides—2'-fucosyllactose, 6'-sialyllactose, and lacto-N-tetraose—showing for each oligosaccharide the constituent monosaccharides added to the lactose disaccharide core to form the full compound. From the structures of FIG. 1 it can be seen that to produce a large range of human milk oligosaccharides, it is necessary to generate activated forms of all five of the aforementioned monosaccharides. The five activated sugars—UDP-glucose, UDP galactose, UDP-N-acetyl-glucosamine, CMP-sialic acid, and GDP-fucose—are used in combination with lactose for the derivation of all human milk oligosaccharides.

Figure 2:
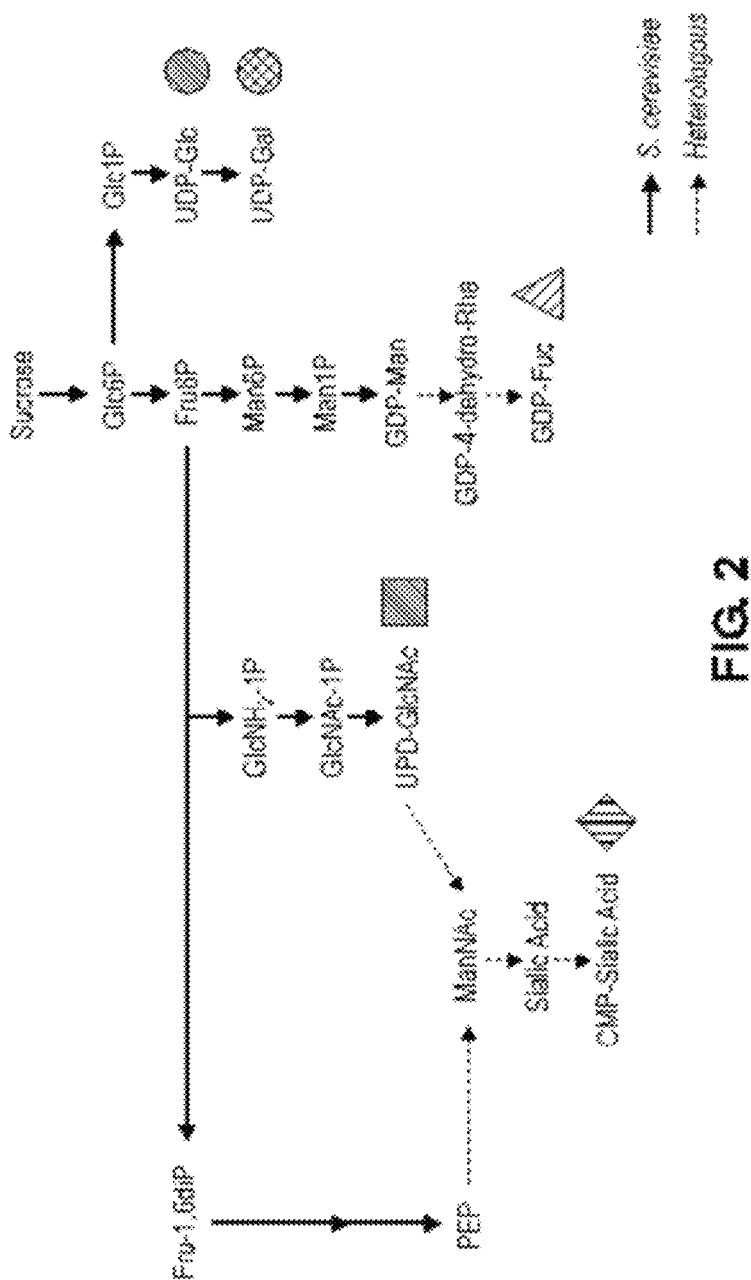
FIG. 2 illustrates biosynthetic pathways for activated sugars used in the formation of human milk oligosaccharides.

FIG. 2 illustrates a network of synthetic pathways of the activated monosaccharides within a cell. As is shown in the illustration, biosynthesis of the activated sugars in a microorganism such as *Saccharomyces cerevisiae* yeast requires a combination of metabolic steps (shown as thick arrows in FIG. 2) that are native to the yeast, and non-native steps (shown as thin arrows in FIG. 2) that require heterologous expression of genes from other organisms. Thus, production of human milk oligosaccharides within a microorganism such as yeast requires, at a minimum, extensive genetic modification and manipulation of the microorganism.

Despite this obstacle to human milk oligosaccharide biosynthesis using the pathways of FIG. 2, no practical alternative route exists for commercial applications. Some sugars, such as fucose and sialic acid, are not commercially available at the quantities required for industrial scale. Furthermore, the synthetic production of activated forms of these sugars is cost prohibitive. For example, the least expensive current commercially available GDP-fucose has a cost of approximately $73/mg. Moreover, even if the costs of these activated sugars were not an important consideration, the import of the sugars across the cellular membrane to be used as substrates for human milk oligosaccharide formation is either not understood or occurs at a rate too low to provide required overall production rates.

Conventional genetically modified microorganisms have been applied to the production of some human milk oligosaccharides, but these demonstrations almost exclusively use microbial host cells, such as *Escherichia coli*. While it has been speculated that these conventional approaches could be applied to similarly engineer more industrially attractive yeast host cells, attempts to do so have been heretofore unsuccessful. To date, the only currently reported production of a human milk oligosaccharide in yeast relies on an alternate synthetic pathway in which exogenous fucose must be supplied to the cells in the form of a medium component (Yu et al., Microb. Cell Fact. 17: 101 (2018)). For reasons discussed above, such a fucose feeding approach is unlikely to be suitable for commercial or industrial purposes.

The inventors have now discovered particular genetic modifications and fermentation methods that enable yeast cells to produce a variety of human milk oligosaccharides. Importantly, this production can be carried out in the absence of exogenous fucose, and has been demonstrated at high yields and productivities. In particular, the genetically modified yeast cells disclosed herein use the pathways outlined in FIG. 3 to synthesize the activated sugars CMP sialic acid, UDP-glucose, UDP-N-acetyl-glucosamine, UDP-galactose, and GDP fucose, as well as human milk oligosaccharides such as 2'-fucosyllactose, 3-fucosyllactose, difucosyllactose, lacto-N-tetraose, lacto-N-neotetraose, 3'-sialyllactose, and 6'-sialyllactose. Advantageously, the provided yeast cells can produce multiple human milk oligosaccharides in a single fermentation by a single strain. Furthermore, the inventors have found that the relative amounts of such co-produced human milk oligosaccharides can be adjusted, e.g., during an operating fermentation, by altering the ratio of carbon sources fed to the yeast culture. Further advantages are realized by applying the recovery methods disclosed herein to obtain high percentages of the produced human milk oligosaccharides.

II. Definitions

The abbreviations used herein have their conventional meaning within the chemical and biological arts.

As used in this specification and the appended claims, the singular forms "a," "an," and "the" include plural reference unless the context clearly dictates otherwise.

As used herein, the term "human milk oligosaccharide" refers to a sugar molecule that is naturally found predominantly or exclusively in human breast milk.

As used herein, the terms "nucleic acid" or "nucleotide" refer to deoxyribonucleic acids (DNA) or ribonucleic acids (RNA) and polymers thereof in either single- or double-stranded form. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

As used herein, the term "gene" refers to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, gRNA, or micro RNA As used herein, the terms "polypeptide," "peptide," and "protein" are used interchangeably to refer to a polymer of amino acid residues. The terms encompass amino acid chains of any length, including full-length proteins, wherein the amino acid residues are linked by covalent peptide bonds.

As used herein the term "heterologous" refers to what is not normally found in nature. The term "heterologous nucleic acid" refers to a nucleic acid not normally found in a given cell in nature. As such, a heterologous nucleic acid can be: (a) foreign to its host cell (i.e., is exogenous to the cell); (b) naturally found in the host cell (i.e., endogenous) but present at an unnatural quantity in the cell (i.e., greater or lesser quantity than naturally found in the host cell); or (c) be naturally found in the host cell but positioned outside of its natural locus.

As used herein, the term "introducing" in the context of introducing a nucleic acid or protein into a host cell refers to any process that results in the presence of a heterologous nucleic acid or polypeptide inside the host cell. For example, the term encompasses introducing a nucleic acid molecule (e.g., a plasmid or a linear nucleic acid) that encodes the nucleic acid of interest (e.g., an RNA molecule) or polypeptide of interest and results in the transcription of the RNA molecules and translation of the polypeptides. The term also encompasses integrating the nucleic acid encoding the RNA molecules or polypeptides into the genome of a progenitor cell. The nucleic acid is then passed through subsequent generations to the host cell, so that, for example, a nucleic acid encoding an RNA-guided endonuclease is "pre-integrated" into the host cell genome. In some cases, introducing refers to translocation of a nucleic acid or polypeptide from outside the host cell to inside the host cell. Various methods of introducing nucleic acids, polypeptides and other biomolecules into host cells are contemplated, including but not limited to, electroporation, contact with nanowires or nanotubes, spheroplasting, PEG 1000-mediated transformation, biolistics, lithium acetate transformation, lithium chloride transformation, and the like.

As used herein, the term "transformation" refers to a genetic alteration of a host cell resulting from the introduction of exogenous genetic material, e.g., nucleic acids, into the host cell.

As used herein, the term "promoter" refers to a nucleic acid control sequences that can direct transcription of a nucleic acid. A promoter includes necessary nucleic acid sequences near the start site of transcription. A promoter also optionally includes distal enhancer or repressor elements, which can be located as much as several thousand base pairs from the start site of transcription.

As used herein, the term "genetic switch" refers to one or more genetic elements that allow controlled expression of enzymes, e.g., enzymes that catalyze the reactions of human milk oligosaccharide biosynthesis pathways. For example, a genetic switch can include one or more promoters operably linked to one or more genes encoding a biosynthetic enzyme, or one or more promoters operably linked to a transcriptional regulator which regulates expression one or more biosynthetic enzymes.

As used herein, the term "operably linked" refers to a functional linkage between nucleic acid sequences such that the sequences encode a desired function. For example, a coding sequence for a gene of interest, e.g., a selectable marker, is in operable linkage with its promoter and/or regulatory sequences when the linked promoter and/or regulatory region functionally controls expression of the coding sequence. It also refers to the linkage between coding sequences such that they may be controlled by the same linked promoter and/or regulatory region; such linkage between coding sequences may also be referred to as being linked in frame or in the same coding frame. "Operably linked" also refers to a linkage of functional but non-coding sequences, such as an autonomous propagation sequence or origin of replication. Such sequences are in operable linkage when they are able to perform their normal function, e.g., enabling the replication, propagation, and/or segregation of a vector bearing the sequence in a host cell.

III. Genetically Modified Yeast

Figure 3:
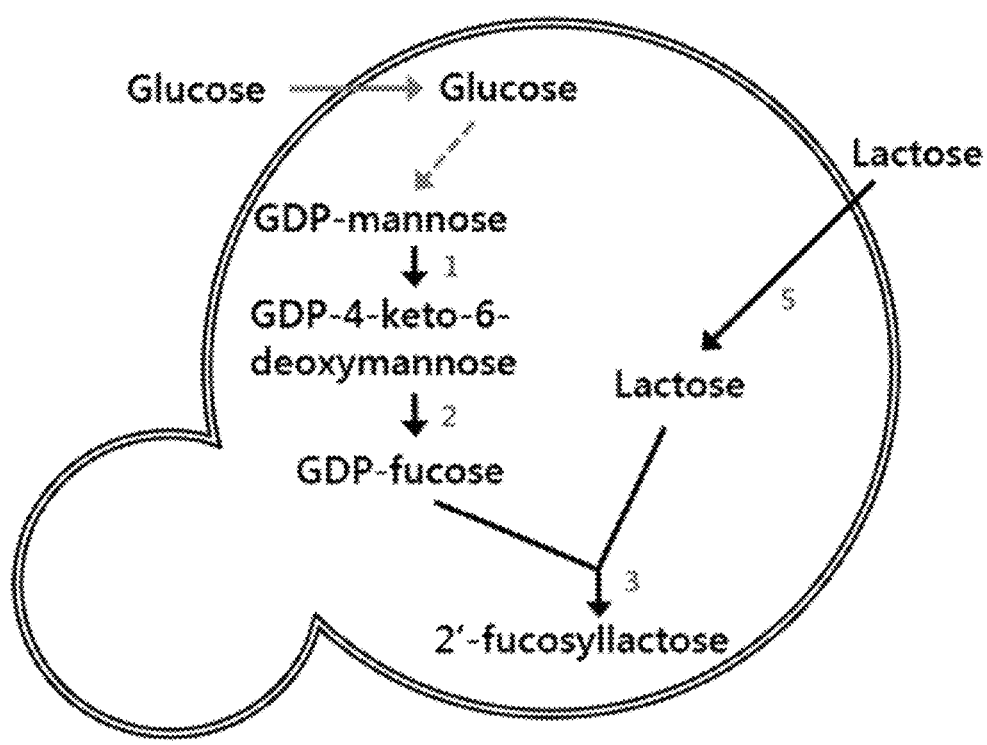
FIG. 3 illustrates the biosynthesis of 2'-fucosyllactose in *Saccharomyces cerevisiae* via attachment of fucose to lactose.

Provided herein are genetically modified yeast cells capable of producing one or more human milk oligosaccharides. The yeast cells include one or more heterologous nucleic acids, each independently encoding an enzyme of a human milk oligosaccharide biosynthetic pathway. As shown in FIG. 3, the biosynthetic pathways of the provided yeast cells generate GDP-fucose from an external sugar such as glucose or sucrose, and not from external fucose. As a result, the genetically modified yeast cells disclosed herein do not include a heterologous nucleic acid encoding a fucokinase, an enzyme used in an alternate pathway converting fucose to GDP-fucose.

The provided genetically modified yeast cells are capable of producing the UDP-glucose human milk oligosaccharide precursor. The activated sugar UDP-glucose consists of a pyrophosphate group, the pentose sugar ribose, glucose, and the nucleobase uracil. UDP-glucose is natively produced by yeast cells, and its production levels can be increased with overexpression of, for example, phosphoglucomutase-2 (PGM2) or UTP glucose-1-phosphate uridylyltransferase (UGP1).

The provided genetically modified yeast cells are capable of producing the UDP-galactose human milk oligosaccharide precursor. The activated sugar UDP-galactose consists of a pyrophosphate group, the pentose sugar ribose, galactose, and the nucleobase uracil. UDP-galactose is natively produced by yeast cells, and its production levels can be increased with overexpression of, for example, UDP-glucose-4-epimerase (GAL10).

The provided genetically modified yeast cells are capable of producing the UDP-N-acetylglucosamine human milk oligosaccharide precursor. The activated sugar UDP-N-acetylglucosamine consists of a pyrophosphate group, the pentose sugar ribose, N-acetylglucosamine, and the nucleobase uracil. UDP-N-acetylglucosamine is natively produced by yeast cells, and its production levels can be increased with expression of, for example, UDP-N-acetylglucosamine-diphosphorylase, or overexpression of, for example, glucosamine 6-phosphate N-acetyltransferase (GNA1) or phosphoacetylglucosamine mutase (PCM1).

The provided genetically modified yeast cells are capable of producing the GDP-fucose human milk oligosaccharide precursor. The activated sugar GDP-fucose consists of a pyrophosphate group, the pentose sugar ribose, fucose, and the nucleobase guanine. GDP-fucose is not natively produced by yeast cells, and its production can be enabled with the introduction of, for example, GDP-mannose 4,6-dehydratase, e.g., from *Escherichia coli*, and GDP-L-fucose synthase, e.g., from *Arabidopsis thaliana*.

The provided genetically modified yeast cells are capable of producing the CMP-sialic acid human milk oligosaccharide precursor. The activated sugar CMP-sialic acid consists of a pyrophosphate group, the pentose sugar ribose, sialic acid, and the nucleobase cytosine. CMP-sialic acid is not natively produced by yeast cells, and its production can be enabled with the introduction of, for example, CMP-Neu5Ac synthetase, e.g., from *Campylobacter jejuni*, sialic acid synthase, e.g., from *C. jejuni*, and UDP-N-acetylglucosamine 2-epimerase, e.g., from *C. jejuni*.

In some embodiments, the genetically modified yeast is capable of producing 2'-fucosyllactose. In addition to one or more heterologous nucleic acids encoding one or more of the aforementioned enzymes, the yeast can further include one or more heterologous nucleic acids encoding one or more of GDP-mannose 4,6-dehydratase, e.g., from *Escherichia coli*, GDP-L-fucose synthase, e.g., from *Arabidopsis thaliana*, a-1,2-fucosyltransferase, e.g., from *Helicobacter pylori*, and a fucosidase, e.g., an α-1,3-fucosidase.

In some embodiments, the genetically modified yeast cell includes a heterologous nucleic acid encoding an enzyme that can catalyze the conversion of GDP-mannose to GDP-4-dehydro-6-deoxy-D-mannose, e.g., a GDP-mannose 4,6-dehydratase. In some embodiments, the GDP-mannose 4,6-dehydratase is from *Escherichia coli*. Other suitable GDP-mannose 4,6-dehydratase sources include, for example and without limitation, *Caenorhabditis elegans*, *Homo sapiens*, *Arabidopsis thaliana*, *Dictyostelium discoideum*, *Mus musculus*, *Drosophila melanogaster*, *Sinorhizobium fredii* HH103, *Sinorhizobium fredii* NGR234, Planctomycetes bacterium RBG_13_63_9 *Silicibacter* sp. TrichCH4B, *Pandoraea vervacti*, *Bradyrhizobium* sp. YR681, *Epulopiscium* sp. SCG-B11WGA-EpuloA1, *Caenorhabditis briggsae*, Candidatus Curtissbacteria bacterium RIFCSPLOWO2_12 FULL_38_9 *Pseudomonas* sp. EpS/L25, *Clostridium* sp. KLE 1755, mine drainage metagenome, *Nitrospira* sp. SGbin2, *Cricetulus griseus*, *Arthrobacter siccitolerans*, and *Paraburkholderia piptadeniae*.

In some embodiments, the genetically modified yeast cell includes a heterologous nucleic acid encoding an enzyme that can catalyze the conversion of GDP-4-dehydro-6-deoxy-D-mannose to GDP-L-fucose, e.g., a GDP-L-fucose synthase. In some embodiments, the GDP-L-fucose synthase is from *Arabidopsis thaliana*. Other suitable GDP-L-fucose synthase sources include, for example and without limitation, *Mus musculus*, *Escherichia coli* K-12, *Homo sapiens*, *Marinobacter salarius*, *Sinorhizobium fredii* NGR234, *Oryza sativa Japonica* Group, *Micavibrio aeruginosavorus* ARL-13, *Citrobacter* sp. 86, *Pongo abelii*, *Caenorhabditis elegans*, Candidatus Staskawiczbacteria bacterium RIFCSPHIGHO2_01_FULL_41_41, *Drosophila melanogaster*, *Azorhizobium caulinodans* ORS 571, Candidatus *Nitrospira nitrificans*, *Mycobacterium elephantis*, Elusimicrobia bacterium RBG_16_66_12, *Vibrio* sp. JCM 19231, *Planktothrix serta* PCC 8927, *Thermodesulfovibrio* sp. RBG_19FT_COMBO_42_12, *Anaerovibrio* sp. JCB, *Dictyostelium discoideum*, and *Cricetulus griseus*.

In some embodiments, the genetically modified yeast cell includes a heterologous nucleic acid encoding an enzyme that can catalyze the conversion of GDP-L-fucose and lactose to 2'-fucosyllactose, e.g., an α-1,2-fucosyltransferase. In some embodiments, the α-1,2-fucosyltransferase is from *Helicobacter pylori*. Other suitable α-1,2-fucosyltransferase sources include, for example and without limitation, *Escherichia coli*, *Sus scrofa*, *Homo sapiens*, *Chlorocebus sabaeus*, *Pan troglodytes*, *Gorilla gorilla gorilla*, *Macaca mulatta*, *Oryctolagus cuniculus*, *Pongo pygmaeus*,

*Mus musculus, Rattus norvegicus, Caenorhabditis elegans, Hylobates lar, Bos taurus, Hylobates agilis, Eulemur fulvus,* and *Helicobacter hepaticus* ATCC 51449.

In some embodiments, the genetically modified yeast cell includes a heterologous nucleic acid encoding an enzyme that can catalyze the conversion of difucosyllactose to 2'-fucosyllactose and fucose, e.g., an α1-3,4-fucosidase. Suitable α1-3,4-fucosidase sources include, for example and without limitations, *Bacteroides thetaiotaomicron, Bifidobacterium bifidum, Bifidobacterium longum, Bifidobacterium longum* subsp. *infantis, Clostridium perfringens, Lactobacillus casei, Paenibacillus thiaminolyticus, Pseudomonas putida, Thermotoga maritima, Xanthomonas campestris* pv. *campestris, Arabidopsis thaliana,* and *Rattus norvegicus.*

In some embodiments, the genetically modified yeast is capable of producing 3-fucosyllactose. In addition to one or more heterologous nucleic acids encoding one or more of the aforementioned enzymes, the yeast can further include one or more heterologous nucleic acids encoding one or more of GDP-mannose 4,6-dehydratase, e.g., from *Escherichia coli,* GDP-L-fucose synthase, e.g., from *Arabidopsis thaliana,* a-1,3-fucosyltransferase, e.g., from *Helicobacter pylori,* and a fucosidase, e.g., an α-1,2-fucosidase.

In some embodiments, the genetically modified yeast cell includes a heterologous nucleic acid encoding an enzyme that can catalyze the conversion of GDP-L-fucose and lactose to 3-fucosyllactose, e.g., an α-1,3-fucosyltransferase. In some embodiments, the α-1,3-fucosyltransferase is from *Helicobacter pylori.* Other suitable α-1,3-fucosyltransferase sources include, for example and without limitation, *Homo sapiens, Escherichia coli, Sus scrofa, Chlorocebus sabaeus, Pan troglodytes, Gorilla gorilla gorilla, Macaca mulatta, Oryctolagus cuniculus, Pongo pygmaeus, Mus musculus, Rattus norvegicus, Caenorhabditis elegans, Hylobates lar, Bos taurus, Hylobates agilis, Eulemur fulvus,* and *Helicobacter hepaticus* ATCC 51449.

In some embodiments, the genetically modified yeast is capable of producing lacto-N-tetraose. In addition to one or more heterologous nucleic acids encoding one or more of the aforementioned enzymes, the yeast can further include one or more heterologous nucleic acids encoding one or more of β-1,3-N-acetylglucosaminyltransferase, e.g., from *Neisseria meningitidis,* β-1,3-galactosyltransferase, e.g., from *Escherichia coli,* and UDP-N-acetylglucosamine-diphosphorylase, e.g., from *E. coli.*

In some embodiments, the genetically modified yeast cell includes a heterologous nucleic acid encoding an enzyme that can catalyze the conversion of UDP-N-acetyl-alpha-D-glucosamine and lactose to lacto-N-triose II and UDP, e.g., a β-1,3-N-acetylglucosaminyltransferase. In some embodiments, the β-1,3-N-acetylglucosaminyltransferase is from *Neisseria meningitidis.* Other suitable β-1,3-N-acetylglucosaminyltransferase sources include, for example and without limitation, *Arabidopsis thaliana, Streptococcus dysgalactiae* subsp. *equisimilis, Escherichia coli* K-12, *Pseudomonas aeruginosa* PAO1, *Homo sapiens, Escherichia coli, Mus musculus, Mycobacterium smegmatis* str. MC2 155, *Dictyostelium discoideum, Komagataeibacter hansenii, Aspergillus nidulans* FGSC A4, *Schizosaccharomyces pombe* 972h-, *Neurospora crassa* OR74A, *Aspergillus fumigatus* Af293, *Ustilago maydis* 521, *Bacillus subtilis* subsp. *subtilis* str. 168, *Rattus norvegicus, Listeria monocytogenes* EGD-e, *Bradyrhizobium japonicum, Nostoc* sp. PCC 7120, *Haloferax volcanii* DS2, *Caulobacter crescentus* CB15, *Mycobacterium avium* subsp. *silvaticum, Oenococcus oeni, Neisseria gonorrhoeae, Propionibacterium freudenreichii* subsp. *shermanii, Escherichia coli* O157:H7, *Aggregatibacter actinomycetemcomitans, Bradyrhizobium diazoefficiens* USDA 110, *Francisella tularensis* subsp. *novicida* U112, *Komagataeibacter xylinus, Haemophilus influenzae* Rd KW20, *Fusobacterium nucleatum* subsp. *nucleatum* ATCC 25586, *Bacillus* phage SPbeta, *Coccidioides posadasii, Populus tremula* x *Populus alba, Rhizopus microsporus* var. *oligosporus, Streptococcus parasanguinis, Shigella flexneri, Caenorhabditis elegans, Hordeum vulgare, Synechocystis* sp. PCC 6803 substr. *Kazusa, Streptococcus agalactiae, Plasmopara viticola, Staphylococcus epidermidis* RP62A, *Shigella* phage SfII, Plasmid pWQ799, *Fusarium graminearum, Sinorhizobium meliloti* 1021, *Physcomitrella patens, Sphingomonas* sp. S88, *Streptomyces hygroscopicus* subsp. *jinggangensis* 5008, *Drosophila melanogaster, Phytophthora infestans, Staphylococcus aureus* subsp. *aureus* Mu50, *Penicillium chrysogenum,* and *Tribolium castaneum.*

In some embodiments, the genetically modified yeast cell includes a heterologous nucleic acid encoding an enzyme that can catalyze the conversion of UDP-galactose and lacto-N-triose II to lacto-N-tetraose and UDP, e.g., a β-1,3-galactosyltransferase. In some embodiments, the β-1,3-galactosyltransferase is from *Escherichia coli.* Other suitable β-1,3-galactosyltransferase sources include, for example and without limitation, *Arabidopsis thaliana, Streptococcus dysgalactiae* subsp. *equisimilis, Pseudomonas aeruginosa* PAO1, *Homo sapiens, Mus musculus, Mycobacterium smegmatis* str. MC2 155, *Dictyostelium discoideum, Komagataeibacter hansenii, Aspergillus nidulans* FGSC A4, *Schizosaccharomyces pombe* 972h-*Neurospora crassa* OR74A, *Aspergillus fumigatus* Af293, *Ustilago maydis* 521, *Bacillus subtilis* subsp. *subtilis* str. 168, *Rattus norvegicus, Neisseria meningitidis, Listeria monocytogenes* EGD-e, *Bradyrhizobium japonicum, Nostoc* sp. PCC 7120, *Haloferax volcanii* DS2, *Caulobacter crescentus* CB15, *Mycobacterium avium* subsp. *silvaticum, Oenococcus oeni, Neisseria gonorrhoeae, Propionibacterium freudenreichii* subsp. *shermanii, Aggregatibacter actinomycetemcomitans, Bradyrhizobium diazoefficiens* USDA 110, *Francisella tularensis* subsp. *novicida* U112, *Komagataeibacter xylinus, Haemophilus influenzae* Rd KW20, *Fusobacterium nucleatum* subsp. *nucleatum* ATCC 25586, *Bacillus* phage SPbeta, *Coccidioides posadasii, Populus tremula* x *Populus alba, Rhizopus microsporus* var. *oligosporus, Streptococcus parasanguinis, Shigella flexneri, Caenorhabditis elegans, Hordeum vulgare, Synechocystis* sp. PCC 6803 substr. *Kazusa, Streptococcus agalactiae, Plasmopara viticola, Staphylococcus epidermidis* RP62A, *Shigella* phage SfII, Plasmid pWQ799, *Fusarium graminearum, Sinorhizobium meliloti* 1021, *Physcomitrella patens, Sphingomonas* sp. S88, *Streptomyces hygroscopicus* subsp. *jinggangensis* 5008, *Drosophila melanogaster, Phytophthora infestans, Staphylococcus aureus* subsp. *aureus* Mu50, *Penicillium chrysogenum,* and *Tribolium castaneum.*

In some embodiments, the genetically modified yeast cell includes a heterologous nucleic acid encoding an enzyme that can catalyze the conversion of N-acetyl-α-D-glucosamine 1-phosphate to UDP-N-acetyl-α-D-glucosamine, e.g., a UDP-N-acetylglucosamine-diphosphorylase. In some embodiments, the UDP-N-acetylglucosamine-diphosphorylase is from *Escherichia coli.*

In some embodiments, the genetically modified yeast is capable of producing lacto-N-neotetraose. In addition to one or more heterologous nucleic acids encoding one or more of the aforementioned enzymes, the yeast can further include one or more heterologous nucleic acids encoding one or more of β-1,3-N-acetylglucosaminyltransferase, e.g., from *Neisseria meningitidis*, β-1,4-galactosyltransferase, e.g., from *N. meningitidis*, and UDP-N-acetylglucosamine-diphosphorylase, e.g., from *E. coli*.

In some embodiments, the genetically modified yeast cell includes a heterologous nucleic acid encoding an enzyme that can catalyze the conversion of UDP-galactose and lacto-N-triose II to lacto N-neotetraose and UDP, e.g., a β-1,4-galactosyltransferase. In some embodiments, the β-1,4-galactosyltransferase is from *Neisseria meningitidis*. Other suitable β-1,4-galactosyltransferase sources include, for example and without limitation, *Homo sapiens*, *Neisseria gonorrhoeae*, *Haemophilus influenzae*, *Acanthamoeba polyphaga* mimivirus, *Haemophilus influenzae* Rd KW20, *Haemophilus ducreyi* 35000HP, *Moraxella catarrhalis*, [*Haemophilus*] *ducreyi*, *Aeromonas salmonicida* subsp. *salmonicida* A449, and *Helicobacter pylori* 26695.

In some embodiments, the genetically modified yeast is capable of producing 3'-sialyllactose. In addition to heterologous nucleic acids encoding one or more of the aforementioned enzymes, the yeast can further include heterologous nucleic acids encoding CMP-Neu5Ac synthetase, e.g., from *Campylobacter jejuni*, sialic acid synthase, e.g., from *C. jejuni*, UDP-N-acetylglucosamine 2-epimerase, e.g., from *C. jejuni*, UDP-N-acetylglucosamine-diphosphorylase, e.g., from *E. coli*, and CMP-N-acetylneuraminate-β-galactosamide-α-2,3-sialyltransferase, e.g., from *N. meningitides* MC58.

In some embodiments, the genetically modified yeast cell includes a heterologous nucleic acid encoding an enzyme that can catalyze the conversion of UDP-N-acetyl-α-D-glucosamine to N-acetyl-mannosamine and UDP, e.g., a UDP-N-acetylglucosamine 2-epimerase. In some embodiments, the UDP-N-acetylglucosamine 2-epimerase is from *Campylobacter jejuni*. Other suitable UDP-N-acetylglucosamine 2-epimerase sources include, for example and without limitation, *Homo sapiens*, *Rattus norvegicus*, *Mus musculus*, *Dictyostelium discoideum*, *Plesiomonas shigelloides*, *Bacillus subtilis* subsp. *subtilis* str. 168, *Bacteroides fragilis*, *Geobacillus kaustophilus* HTA426, *Synechococcus* sp. CC9311, *Sphingopyxis alaskensis* RB2256, *Synechococcus* sp. RS9916, *Moorella thermoacetica* ATCC 39073, *Psychrobacter* sp. 1501(2011), *Zunongwangia profunda* SM-A87, *Thiomicrospira crunogena* XCL-2, *Polaribacter* sp MED152, *Vibrio campbellii* ATCC BAA-1116, *Thiomonas arsenitoxydans*, *Nitrobacter winogradskyi* Nb-255, *Raphidiopsis brookii* D9, *Thermoanaerobacter italicus* Ab9, *Roseobacter litoralis* Och 149, *Halothiobacillus neapolitanus* c2, *Halothiobacillus neapolitanus* c2, *Bacteroides vulgatus* ATCC 8482, *Zunongwangia profunda* SM-A87, *Moorella thermoacetica* ATCC 39073, *Paenibacillus polymyxa* E681, *Desulfatibacillum alkenivorans* AK-01, *Magnetospirillum magneticum* AMB-1, *Thermoanaerobacter italicus* Ab9, *Paenibacillus polymyxa* E681, *Prochlorococcus marinus* str. MIT 9211, *Subdoligranulum variabile* DSM 15176, *Kordia algicida* OT-1, *Bizionia argentinensis* JUB59, *Tannerella forsythia* 92A2, *Thiomonas arsenitoxydans*, *Synechococcus* sp. BL107, *Escherichia coli*, *Vibrio campbellii* ATCC BAA-1116, *Rhodopseudomonas palustris* HaA2, *Roseobacter litoralis* Och 149, *Synechococcus* sp. CC9311, *Subdoligranulum variabile* DSM 15176, *Bizionia argentinensis* JUB59, *Selenomonas* sp. oral taxon 149 str. 67H29BP, *Bacteroides vulgatus* ATCC 8482, *Kordia algicida* OT-1, *Desulfatibacillum alkenivorans* AK-01, *Thermodesulfovibrio yellowstonii* DSM 11347, *Desulfovibrio aespoeensis* Aspo-2, *Synechococcus* sp. BL107, and *Desulfovibrio aespoeensis* Aspo-2.

In some embodiments, the genetically modified yeast cell includes a heterologous nucleic acid encoding an enzyme that can catalyze the conversion of N-acetyl-mannosamine and phosphoenolpyruvate to N-acetylneuraminate, e.g., a sialic acid synthase. In some embodiments, the sialic acid synthase is from *Campylobacter jejuni*. Other suitable sialic acid synthase sources include, for example and without limitation, *Homo sapiens*, groundwater metagenome, *Prochlorococcus marinus* str. MIT 9211, *Rhodospirillum centenum* SW, *Rhodobacter capsulatus* SB 1003, *Aminomonas paucivorans* DSM 12260, *Ictalurus punctatus*, *Octadecabacter antarcticus* 307, *Octadecabacter arcticus* 238, *Butyrivibrio proteoclasticus* B316, and *Neisseria meningitidis* serogroup B.

In some embodiments, the genetically modified yeast cell includes a heterologous nucleic acid encoding an enzyme that can catalyze the conversion of N-acetylneuraminate and CTP to CMP-N-acetylneuraminate, e.g., a CMP-Neu5Ac synthetase. In some embodiments, the CMP-Neu5Ac synthetase is from *Campylobacter jejuni*. Other suitable CMP-Neu5Ac synthetase sources include, for example and without limitation, *Neisseria meningitidis*, *Streptococcus agalactiae* NEM316, *Homo sapiens*, *Mus musculus*, *Bacteroides thetaiotaomicron*, *Pongo abelii*, *Danio rerio*, *Oncorhynchus mykiss*, *Bos taurus*, *Drosophila melanogaster*, and *Streptococcus suis* BM407.

In some embodiments, the genetically modified yeast cell includes a heterologous nucleic acid encoding an enzyme that can catalyze the conversion of CMP-N-acetylneuraminate and lactose to 3'-siallyllactose and CMP, e.g., a CMP-N-acetylneuraminate-β-galactosamide-α-2,3-sialyltransferase. In some embodiments, the CMP-N-acetylneuraminate-β-galactosamide-α-2,3-sialyltransferase is from *N. meningitides* MC58. Other suitable CMP-N-acetylneuraminate-β-galactosamide-α-2,3-sialyltransferase sources include, for example and without limitation, *Homo sapiens*, *Neisseria meningitidis* alpha14, *Pasteurella multocida* subsp. *multocida* str. Pm70, *Pasteurella multocida*, and *Rattus norvegicus*.

In some embodiments, the genetically modified yeast is capable of producing 6'-sialyllactose. In addition to one or more heterologous nucleic acids encoding one or more of the aforementioned enzymes, the yeast can further include one or more heterologous nucleic acids encoding one or more of CMP-Neu5Ac synthetase, e.g., from *Campylobacter jejuni*, sialic acid synthase, e.g., from *C. jejuni*, UDP-N-acetylglucosamine 2-epimerase, e.g., from *C. jejuni*, UDP-N-acetylglucosamine-diphosphorylase, e.g., from *E. coli*, and β-galactoside α-2,6-sialyltransferase, e.g., from *Photobacterium* sp. JT-ISH-224.

In some embodiments, the genetically modified yeast cell includes a heterologous nucleic acid encoding an enzyme that can catalyze the conversion of CMP-N-acetylneuraminate and lactose to 3'siallyllactose and CMP, e.g., a β-galactoside-α-2,6-sialyltransferase. In some embodiments, the β-galactoside-α-2,6-sialyltransferase is from *Photobacterium* sp. JT-ISH-224. Other suitable β-galactoside-α-2,6-sialyltransferase sources include, for example and without limitation, *Homo sapiens*, *Photobacterium damselae*, *Photobacterium leiognathi*, and *Photobacterium phosphoreum* ANT-2200.

In some embodiments, the genetically modified yeast cell is *Saccharomyces cerevisae*. *Saccharomyces cerevisae* strains suitable for genetic modification and cultivation to produce human milk oligosaccharides as disclosed herein include, but are not limited to, Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, CEN.PK, CEN.PK2, and AL-1. In some embodiments, the host cell is a strain of *Saccharomyces cerevisiae* selected from the group consisting of PE-2, CAT-1, VR-1, BG-1, CR-1, and SA-1. In certain aspects, the strain of *Saccharomyces cerevisiae* is PE-2. In certain embodiments, the strain of *Saccharomyces cerevisiae* is CAT-1. In some aspects, the strain of *Saccharomyces cerevisiae* is BG-1.

In some embodiments, the genetically modified yeast cell is *Saccharomyces cerevisiae*, and in addition to heterologous nucleic acids encoding one or more of the aforementioned enzymes, the yeast can further include a heterologous nucleic acid encoding a lactose transporter. In some embodiments, the lactose transporter is a lactose permease, e.g., LAC12 from *Kluyveromyces lactis*. Other suitable lactose permease sources include, for example and without limitation, *Scheffersomyces stipitis, Aspergillus lentulus, Emericella nidulans, Dacryopinax primogenitus, Microdochium bolleyi, Beauveria bassiana, Metarhizium robertsii, Phialocephala, Botryosphaeria parva, Monthophthora roreri, Cordyceps fumosorosea, Diplodia seriata, Hypocrea jecorina, Neurospora crassa*, and *Kluyveromyces marxianus*.

In some embodiments, the genetically modified yeast cell is *Kluyveromyces marxianus*. *Kluyveromyces marxianus* can present several advantages for industrial production, including high temperature tolerance, acid tolerance, native uptake of lactose, and rapid growth rate. Beneficially, this yeast is genetically similar enough to *Saccharomyces cerevisiae* that similar or identical promoters and codon optimized genes can be used among the two yeast species. Furthermore, because *Kluyveromyces marxianus* has a native lactose permease, it is not necessary to introduce a heterologous nucleic acid to introduce this functionality. In some embodiments, at least a portion of the β-galactosidase gene (LAC4) required for metabolizing lactose is deleted in the genetically modified yeast. Thus, the modified *Kluyveromyces marxianus* strain is capable of importing lactose without consuming it. In some embodiments, the expression of the β-galactosidase gene in the genetically modified yeast is decreased relative to the expression in wild-type *Kluyveromyces marxianus*. Thus, the modified *Kluyveromyces marxianus* strain has reduced consumption of imported lactose.

In some embodiments, the genetically modified yeast cell includes a promoter that regulates the expression and/or stability of at least one of the one or more heterologous nucleic acids. In certain aspects, the promoter negatively regulates the expression and/or stability of the at least one heterologous nucleic acid. The promoter can be responsive to a small molecule that can be present in the culture medium of a fermentation of the modified yeast. In some embodiments, the small molecule is maltose or an analog or derivative thereof. In some embodiments, the small molecule is lysine or an analog or derivative thereof. Maltose and lysine can be attractive selections for the small molecule as they are relatively inexpensive, non-toxic, and stable.

The yeast cells disclosed herein can be genetically engineered to comprise one or more of the modifications described above, e.g., one or more heterologous nucleic acids encoding biosynthetic pathway enzymes, e.g., for the production of one or more human milk oligosaccharides. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell.

In some embodiments, the one or more heterologous nucleic acids are introduced into the genetically modified yeast cells by using a gap repair molecular biology technique. In these methods, if the yeast has non-homologous end joining (NHEJ) activity, as is the case for *Kluyveromyces marxianus*, then the NHEJ activity in the yeast can be first disrupted in any of a number of ways. Further details related to genetic modification of yeast cells through gap repair can be found in U.S. Pat. No. 9,476,065, the full disclosure of which is incorporated by reference herein in its entirety for all purposes.

In some embodiments, the one or more heterologous nucleic acids are introduced into the genetically modified yeast cells by using one or more site-specific nucleases capable of causing breaks at designated regions within selected nucleic acid target sites. Examples of such nucleases include, but are not limited to, endonucleases, site-specific recombinases, transposases, topoisomerases, zinc finger nucleases, TAL-effector DNA binding domain-nuclease fusion proteins (TALENs), CRISPR/Cas-associated RNA-guided endonucleases, and meganucleases. Further details related to genetic modification of yeast cells through site specific nuclease activity can be found in U.S. Pat. No. 9,476,065, the full disclosure of which is incorporated by reference herein in its entirety for all purposes.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art. Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias."

Optimized coding sequences containing codons preferred by a particular prokaryotic or eukaryotic host (Murray et al., 1989, Nucl Acids Res. 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E.* coli commonly use UAA as the stop codon (Dalphin et al., 1996, Nucl Acids Res. 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes, e.g., gaps can be introduced in one or both of a first and a second amino acid or nucleic acid sequence for optimal alignment and non-homologous sequences can be disregarded for comparison purposes. In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties, e.g., charge or hydrophobicity. In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, Methods in Mol. Biol. 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used for comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof) can be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y.* spp. *Torulaspora pretoriensis*, *Issatchenkia orientalis*, *Schizosaccharomyces* spp., including *S. pombe*, *Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., *Salmonella* spp., or *X dendrorhous*.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art can be suitable to identify analogous genes and analogous enzymes. Techniques include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, e.g., as described herein or in Kiritani, K., Branched-Chain Amino Acids Methods Enzymology, 1970; then isolating the enzyme with said activity through purification; determining the protein sequence of the enzyme through techniques such as Edman degradation; design of PCR primers to the likely nucleic acid sequence; amplification of said DNA sequence through PCR; and cloning of said nucleic acid sequence. To identify homologous or similar genes and/or homologous or similar enzymes, suitable techniques also include comparison of data concerning a candidate gene or enzyme with databases such as BRENDA, KEGG, or MetaCYC. The candidate gene or enzyme can be identified within the above mentioned databases in accordance with the teachings herein.

IV. Methods of Producing Human Milk Oligosaccharides

Also provided herein are methods of producing one or more human milk oligosaccharides. The methods include providing a population of genetically modified yeast cells capable of producing one or more human milk oligosaccharides. Each yeast cell of the population can include one more heterologous nucleic acids that encode an enzyme of a human milk oligosaccharide biosynthetic pathway. In some embodiments, the population includes any of the yeast cells as disclosed herein and discussed above. The methods further include providing a culture medium, and culturing the yeast cells in the culture medium under conditions suitable for the yeast cells to produce the one or more milk oligosaccharides.

The culturing can be performed in a suitable culture medium in a suitable container, including but not limited to a cell culture plate, a flask, or a fermentor. Any suitable fermentor may be used, including, but not limited to, a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric et al., in Ullmann's Encyclopedia of Industrial Chemistry, Sixth Edition, Volume 12, pages 398-473, Wiley-VCH Verlag GmbH & Co. KDaA, Weinheim, Germany. Further, the methods can be performed at any scale of fermentation known in the art to support industrial production of microbial products. Materials and methods for the maintenance and growth of cell cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

In some embodiments, the culturing is carried out for a period of time sufficient for the transformed population to undergo a plurality of doublings until a desired cell density is reached. In some embodiments, the culturing is carried out for a period of time sufficient for the host cell population to reach a cell density (OD600) of between 0.01 and 400 in the fermentation vessel or container in which the culturing is being carried out. The culturing can be carried out until the cell density is, for example, between 0.1 and 14, between 0.22 and 33, between 0.53 and 76, between 1.2 and 170, or between 2.8 and 400. In terms of upper limits, the culturing can be carried until the cell density is no more than 400, e.g., no more than 170, no more than 76, no more than 33, no more than 14, no more than 6.3, no more than 2.8, no more than 1.2, no more than 0.53, or no more than 0.23. In terms of lower limits, the culturing can be carried out until the cell density is greater than 0.1, e.g., greater than 0.23, greater than 0.53, greater than 1.2, greater than 2.8, greater than 6.3, greater than 14, greater than 33, greater than 76, or greater than 170. Higher cell densities, e.g., greater than 400, and lower cell densities, e.g., less than 0.1, are also contemplated.

In other embodiments, the culturing is carried for a period of time, for example, between 12 hours and 92 hours, e.g., between 12 hours and 60 hours, between 20 hours and 68 hours, between 28 hours and 76 hours, between 36 hours and 84 hours, or between 44 hours and 92 hours. In some embodiments, the culturing is carried out for a period of time, for example, between 5 days and 20 days, e.g., between 5 days and 14 days, between 6.5 days and 15.5 days, between 8 days and 17 days, between 9.5 days and 18.5 days, or between 11 days and 20 days. In terms of upper limits, the culturing can be carried out for less than 20 days, e.g., less than 18.5 days, less than 17 days, less than 15.5 days, less than 14 days, less than 12.5 day, less than 11 days, less than 9.5 days, less than 8 days, less than 6.5 days, less than 5 day, less than 92 hours, less than 84 hours, less than 76 hours, less than 68 hours, less than 60 hours, less than 52 hours, less than 44 hours, less than 36 hours, less than 28 hours, or less than 20 hours. In terms of lower limits, the culturing can be carries out for greater than 12 hours, e.g., greater than 20 hours, greater than 28 hours, greater than 36 hours, greater than 44 hours, greater than 52 hours, greater than 60 hours, greater than 68 hours, greater than 76 hours, greater than 84 hours, greater than 92 hours, greater than 5 days, greater than 6.5 days, greater than 8 days, greater than 9.5 days, greater than 11 days, greater than 12.5 days, greater than 14 days, greater than 15.5 days, greater than 17 days, or greater than 18.5 days. Longer culturing times, e.g., greater than 20 days, and shorter culturing times, e.g., less than 5 hours, are also contemplated.

In certain embodiments, the production of the one or more human milk oligosaccharides by the population of genetically modified yeast is inducible by an inducing compound. Such yeast can be manipulated with ease in the absence of the inducing compound. The inducing compound is then added to induce the production of the human milk oligosaccharides by the yeast. In other embodiments, production of the one or more human milk oligosaccharides by the yeast is inducible by changing culture conditions, such as, for example, the growth temperature, media constituents, and the like.

In certain embodiments, an inducing agent is added during a production stage to activate a promoter or to relieve repression of a transcriptional regulator associated with a biosynthetic pathway to promote production of human milk oligosaccharides. In certain embodiments, an inducing agent is added during a build stage to repress a promoter or to activate a transcriptional regulator associated with a biosynthetic pathway to repress the production of human milk oligosaccharides, and an inducing agent is removed during the production stage to activate a promoter to relieve repression of a transcriptional regulator to promote the production of human milk oligosaccharides. The term "genetic switch" is used herein to refer to the use of a promoter or other genetic elements to control activation or de-activation of the biosynthetic pathway for the one or more human milk oligosaccharides. Illustrative examples of useful inducing agents or genetic switches are described in, e.g., PCT Application Publications WO2015/020649, WO2016/210343, and WO2016210350, which are incorporated herein by reference in their entirety.

As discussed above, in some embodiments, the provided genetically modified yeast cell includes a promoter that regulates the expression and/or stability of at least one of the one or more heterologous nucleic acids. Thus, in certain embodiments, the promoter can be used to control the timing of gene expression and/or stability of proteins, for example, enzymes of a biosynthetic pathway for producing human milk oligosaccharides in genetically modified yeast cells during fermentation.

In some embodiments, when fermentation of a genetically modified yeast cell is carried out in the presence of a small molecule, e.g., at least about 0.1% maltose or lysine, human milk oligosaccharide production is substantially reduced or turned off. When the amount of the small molecule in the fermentation culture medium is reduced or eliminated, human milk oligosaccharide production is turned on or increased. Such a system enables the use of the presence or concentration of a selected small molecule in a fermentation medium as a switch for the production of non-catabolic, e.g., human milk oligosaccharide, compounds. Controlling the timing of non-catabolic compound production to occur only when production is desired redirects the carbon flux during the non-production phase into cell maintenance and biomass. This more efficient use of carbon can greatly reduce the metabolic burden on the host cells, improve cell growth, increase the stability of the heterologous genes, reduce strain degeneration, and/or contribute to better overall health and viability of the cells.

In some embodiments, the fermentation method comprises a two-step process that utilizes a small molecule as a switch to effect the "off" and "on" stages. In the first step, i.e., the "build" stage, step (a) wherein production of the compound is not desired, the genetically modified yeast are grown in a growth or "build" medium comprising the small molecule in an amount sufficient to induce the expression of genes under the control of a responsive promoter, and the induced gene products act to negatively regulate production of the non-catabolic compound. After transcription of the fusion DNA construct under the control of a maltose-responsive or lysine-responsive promoter, the stability of the fusion proteins is post-translationally controlled. In the second step, i.e., the "production" stage, step (b), the fermentation is carried out in a culture medium comprising a carbon source wherein the small molecule is absent or in sufficiently low amounts such that the activity of a responsive promoter is reduced or inactive and the fusion proteins are destabilized. As a result, the production of the heterologous non-catabolic compound by the host cells is turned on or increased.

In other embodiments, a responsive promoter can be operably linked to one or more heterologous nucleic acids encoding one or more enzymes of a human milk oligosaccharide pathway. The presence of an activating amount of the small molecule in the culture medium increases the expression of the one or more enzymes of the biosynthetic pathway. In these embodiments, the presence of a sufficient amount of maltose or lysine in the culture medium will increase expression of one or more enzymes of the biosynthetic pathway, and the fusion enzymes are stabilized in the presence of the small molecule.

In some embodiments, the culture medium is any culture medium in which a genetically modified yeast capable of producing an human milk oligosaccharide can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

In another embodiment, the method of producing human milk oligosaccharides comprises culturing host cells in separate build and production culture media. For example, the method can comprise culturing the genetically modified host cell in a build stage wherein the cell is cultured under non-producing conditions, e.g., non-inducing conditions, to produce an inoculum, then transferring the inoculum into a second fermentation medium under conditions suitable to induce human milk oligosaccharide production, e.g., inducing conditions, and maintaining steady state conditions in the second fermentation stage to produce a cell culture containing human milk oligosaccharides.

In some embodiments, the culture medium comprises sucrose and lactose. In some embodiments, the carbon sources in the culture medium consist essentially of sucrose and lactose. In some embodiments, the carbon sources in the culture medium consist of sucrose and lactose. In some embodiments, the mass ratio of the sucrose to the lactose is selected to influence, adjust, or control the relative production rates of human milk oligosaccharides produced by the yeast cells. Controlling the composition of the produced human milk oligosaccharides in this way can advantageously permit the increasing of desired products, the decreasing of undesired products, the targeting of a desired product ratio, and the simplification of downstream product separation processes.

The mass ratio of the sucrose to the lactose in the culture medium can be, for example, between 4 and 40, e.g., between 4 and 25.6, between 7.6 and 29.2, between 11.2 and 32.8, between 14.8 and 36.4, or between 18.4 and 40. In terms of upper limits, the mass ratio of the sucrose to the lactose can be less than 40, e.g., less than 36.4, less than 32.8, less than 29.2, less than 25.6, less than 22, less than 18.4, less than 14.8, less than 11.2, or less than 7.6. In terms of lower limits, the mass ratio of the sucrose to the lactose can be greater than 4, e.g., greater than 7.6, greater than 11.2, greater than 14.8, greater than 18.4, greater than 22, greater than 25.6, greater than 29.2, greater than 32.8, or greater than 36.4. Higher ratios, e.g., greater than 40, and lower ratios, e.g., less than 4, are also contemplated.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. In some embodiments, the addition of a nitrogen source to the culture medium beyond a certain concentration is not advantageous for the growth of the yeast. As a result, the concentration of the nitrogen sources, in the culture medium can be less than about 20 g/L, e.g., less than about 10 g/L or less than about 5 g/L. Further, in some instances it may be desirable to allow the culture medium to become depleted of the nitrogen sources during culturing.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, e.g., greater than about 2.0 g/L or greater than about 5.0 g/L. In some embodiments, the addition of phosphate to the culture medium beyond certain concentrations is not advantageous for the growth of the yeast. Accordingly, the concentration of phosphate in the culture medium can be less than about 20 g/L, e.g., less than about 15 g/L or less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, e.g., greater than about 1.0 g/L or greater than about 2.0 g/L. In some embodiments, the addition of magnesium to the culture medium beyond certain concentrations is not advantageous for the growth of the yeast. Accordingly, the concentration of magnesium in the culture medium can be less than about 10 g/L, e.g, less than about 5 g/L or less than about 3 g/L. Further, in some instances it may be desirable to allow the culture medium to become depleted of a magnesium source during culturing.

In some embodiments, the culture medium can also include a biologically acceptable chelating agent, such as the dihydrate of trisodium citrate. In such instance, the concentration of a chelating agent in the culture medium can be greater than about 0.2 g/L, e.g., greater than about 0.5 g/L or greater than about 1 g/L. In some embodiments, the addition of a chelating agent to the culture medium beyond certain concentrations is not advantageous for the growth of the yeast. Accordingly, the concentration of a chelating agent in the culture medium can be less than about 10 g/L, e.g., less than about 5 g/L or less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, e.g., within the range of from about 20 mg/L to about 1000 mg/L or in the range of from about 50 mg/L to about 500 mg/L.

The culture medium can also include sodium chloride. Typically, the concentration of sodium chloride in the culture medium is within the range of from about 0.1 g/L to about 5 g/L, e.g., within the range of from about 1 g/L to about 4 g/L or in the range of from about 2 g/L to about 4 g/L.

In some embodiments, the culture medium can also include trace metals. Such trace metals can be added to the culture medium as a stock solution that, for convenience, can be prepared separately from the rest of the culture medium Typically, the amount of such a trace metals solution added to the culture medium is greater than about 1 ml/L, e.g., greater than about 5 mL/L, and more preferably greater than about 10 mL/L. In some embodiments, the addition of a trace metals to the culture medium beyond certain concentrations is not advantageous for the growth of the yeast. Accordingly, the amount of such a trace metals solution added to the culture medium can be less than about 100 mL/L, e.g., less than about 50 mL/L or less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, inositol, pyridoxine-HCl, thiamine-HCl, and combinations thereof. Such vitamins can be added to the culture medium as a stock solution that, for convenience, can be prepared separately from the rest of the culture medium In some embodiments, the addition of vitamins to the culture medium beyond certain concentrations is not advantageous for the growth of the yeast.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, e.g., during the production stage of the fermentation. In some embodiments, the culture may be supplemented with relatively high concentrations of such components at the outset, for example, of the production stage, so that growth and/or human milk oligosaccharide production is supported for a period of time before additions are required. The preferred ranges of these components can be maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those of ordinary skill in the art, the rate of consumption of nutrient increases during culture as the cell density of the medium increases. Moreover, to avoid introduction of foreign microorganisms into the culture medium, addition can be performed using aseptic addition methods, as are known in the art. In addition, a small amount of anti-foaming agent may be added during the culture.

The temperature of the culture medium can be any temperature suitable for growth of the genetically modified yeast population and/or production of the one or more human milk oligosaccharides. For example, prior to inoculation of the culture medium with an inoculum, the culture medium can be brought to and maintained at a temperature in the range of from about 20° C. to about 45° C., e.g., to a temperature in the range of from about 25° C. to about 40° C. or of from about 28° C. to about 32° C.

The pH of the culture medium can be controlled by the addition of acid or base to the culture medium In such cases when ammonia is used to control pH, it also conveniently serves as a nitrogen source in the culture medium In some embodiments, the pH is maintained from about 3.0 to about 8.0, e.g., from about 3.5 to about 7.0 or from about 4.0 to about 6.5.

In some embodiments, the genetically modified yeast cells produce 2'-fucosyllactose. The concentration of produced 2'-fucosyllactose in the culture medium can be, for example, between 5 g/l and 40 g/l, e.g., between 5 g/l and 26 g/l, between 8.5 g/l and 29.5 g/l, between 12 g/l and 33 g/l, between 15.5 g/l and 36.5 g/l, or between 19 g/l and 40 g/l. In terms of upper limits, the 2'-fucosyllactose concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. Higher concentrations, e.g., greater than 40 g/l, are also contemplated.

The yield of produced 2'-fucosyllactose on the sucrose in the culture medium can be, for example, between 0.01 g/g and 0.1 g/g, e.g., between 0.01 g/g and 0.064 g/g, between 0.019 g/g and 0.073 g/g, between 0.028 g/g and 0.082 g/g, between 0.037 g/g and 0.091 g/g, or between 0.046 g/g and 0.1 g/g. In terms of lower limits, the yield of 2'-fucosyllactose on sucrose can be greater than 0.01 g/g, e.g., greater than 0.019 g/g, greater than 0.028 g/g, greater than 0.037 g/g, greater than 0.046 g/g, greater than 0.055 g/g, greater than 0.064 g/g, greater than 0.073 g/g, greater than 0.082 g/g, or greater than 0.091 g/g. Higher yields, e.g., greater than 0.1 g/g, are also contemplated.

In some embodiments, the genetically modified yeast cells produce difucosyllactose. The concentration of produced difucosyllactose in the culture medium can be, for example, between 5 g/l and 40 g/l, e.g., between 5 g/l and 26 g/l, between 8.5 g/l and 29.5 g/l, between 12 g/l and 33 g/l, between 15.5 g/l and 36.5 g/l, or between 19 g/l and 40 g/l. In terms of upper limits, the 2'-fucosyllactose concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. Higher concentrations, e.g., greater than 40 g/l, are also contemplated.

In some embodiments, it is desirable to minimize the amount of difucosyllactose produced by the genetically modified yeast cells relative the amount of 2'-fucosyllactose produced. The mass of difucosyllactose produced by the yeast cells per g of 2'-fucosyllactose produced by the yeast cells can be, for example, between 0.2 g and 4.2 g, e.g., between 0.2 g and 2.6 g, between 0.6 g and 3 g, between 1 g and 3.4 g, between 1.4 g and 3.8 g, or between 1.8 g and 4.2 g. In terms of upper limits, the mass of difucosyllactose produced per g of 2'-fucosyllactose can be less than 4.2 g, e.g., less than 3.8 g, less than 3.4 g, less than 3 g, less than 2.6 g, less than 2.2 g, less than 1.8 g, less than 1.4 g, less than 1 g, less than 0.6 g, or less than 0.2 g. In terms of lower limits, the mass of difucosyllactose produced per g of 2'-fucosyllactose can be greater than 0.2 g, e.g., greater than 0.6 g, greater than 1 g, greater than 1.4 g, greater than 1.8 g, greater than 2.2 g, greater than 2.6 g, greater than 3 g, greater than 3.4 g, or greater than 3.8 g. Higher mass ratios, e.g., greater than 4.2 g/g, and lower mass ratios, e.g., less than 0.2 g/g, are also contemplated.

In some embodiments, the genetically modified yeast cells produce lacto-N-tetraose. The concentration of produced lacto-N-tetraose in the culture medium can be, for example, between 0.5 g/l and 8 g/l, e.g., between 0.5 g/l and 2.6 g/l, between 0.7 g/l and 3.5 g/l, between 0.9 g/l and 4.6 g/l, between 1.1 g/l and 6.1 g/l, or between 1.5 g/l and 8 g/l. In terms of upper limits, the lacto-N-tetraose concentration can be greater than 0.5 g/l, e.g., greater than 0.7 g/l, greater than 0.9 g/l, greater than 1.1 g/l, greater than 1.5 g/l, greater than 2 g/l, greater than 2.6 g/l, greater than 3.5 g/l, greater than 4.6 g/l, or greater than 6 g/l. Higher concentrations, e.g., greater than 8 g/l, are also contemplated.

In some embodiments, the genetically modified yeast cells produce lacto-N-neotetraose. The concentration of produced lacto-N-neotetraose in the culture medium can be, for example, between 0.5 g/l and 30 g/l, e.g., between 0.5 g/l and 5.8 g/l, between 0.8 g/l and 8.8 g/l, between 1.1 g/l and 13 g/l, between 1.7 g/l and 20 g/l, or between 2.6 g/l and 30 g/l. In terms of upper limits, the lacto-N-neotetraose concentration can be greater than 0.5 g/l, e.g., greater than 0.8 g/l, greater than 1.1 g/l, greater than 1.7 g/l, greater than 2.6 g/l, greater than 3.9 g/l, greater than 5.8 g/l, greater than 8.8 g/l, greater than 13 g/l, or greater than 20 g/l. Higher concentrations, e.g., greater than 30 g/l, are also contemplated.

In some embodiments, the genetically modified yeast cells produce 3-fucosyllactose. The concentration of produced 3-fucosyllactose in the culture medium can be, for example, between 0.05 g/l and 0.8 g/l, e.g., between 0.05 g/l and 0.26 g/l, between 0.07 g/l and 0.35 g/l, between 0.09 g/l and 0.46 g/l, between 0.11 g/l and 0.61 g/l, or between 0.15 g/l and 0.8 g/l. In terms of upper limits, the 3-fucosyllactose concentration can be greater than 0.05 g/l, e.g., greater than 0.07 g/l, greater than 0.09 g/l, greater than 0.11 g/l, greater than 0.15 g/l, greater than 0.2 g/l, greater than 0.26 g/l, greater than 0.35 g/l, greater than 0.46 g/l, or greater than 0.6 g/l. Higher concentrations, e.g., greater than 0.8 g/l, are also contemplated.

In some embodiments, the genetically modified yeast cells produce 3'-sialyllactose. The concentration of produced 3'-sialyllactose in the culture medium can be, for example, between 0.1 g/l and 1.6 g/l, e.g., between 0.1 g/l and 0.53 g/l, between 0.13 g/l and 0.7 g/l, between 0.17 g/l and 0.92 g/l, between 0.23 g/l and 1.2 g/l, or between 0.3 g/l and 1.6 g/l. In terms of upper limits, the 3'-sialyllactose concentration can be greater than 0.1 g/l, e.g., greater than 0.13 g/l, greater than 0.17 g/l, greater than 0.23 g/l, greater than 0.3 g/l, greater than 0.4 g/l, greater than 0.53 g/l, greater than 0.7 g/l, greater than 0.92 g/l, or greater than 1.2 g/l. Higher concentrations, e.g., greater than 1.6 g/l, are also contemplated.

In some embodiments, the genetically modified yeast cells produce 6'-sialyllactose. The concentration of produced 6'-sialyllactose in the culture medium can be, for example, between 0.25 g/l and 4 g/l, e.g., between 0.25 g/l and 1.3 g/l, between 0.33 g/l and 1.7 g/l, between 0.44 g/l and 2.3 g/l, between 0.57 g/l and 3.1 g/l, or between 0.76 g/l and 4 g/l. In terms of upper limits, the 3'-sialyllactose concentration can be greater than 0.25 g/l, e.g., greater than 0.33 g/l, greater than 0.44 g/l, greater than 0.57 g/l, greater than 0.76 g/l, greater than 1 g/l, greater than 1.3 g/l, greater than 1.7 g/l, greater than 2.3 g/l, or greater than 3 g/l. Higher concentrations, e.g., greater than 4 g/l, are also contemplated.

V. Fermentation Compositions

Also provided are fermentation compositions including a population of genetically modified yeast cells. The yeast cells can include any of the yeast cells disclosed herein and discussed above. In some embodiments, the fermentation composition further includes at least one human milk oligosaccharide produced from the yeast cells. The at least one human milk oligosaccharide in the fermentation composition can include, for example, 2'-fucosyllactose, difucosyllactose, 3-fucosyllactose, lacto-N-tetraose, lacto-N-neotetraose, 3'-sialyllactose, or 6'-sialyllactose. In some embodiments, the fermentation composition includes at least two human milk oligosaccharides. The at least two human milk oligosaccharides in the fermentation composition can include, for example, 2'-fucosyllactose and difucosyllactose, 2'-fucosyllactose and 3-fucosyllactose, 2'-fucosyllactose and lacto-N-tetraose, 2'-fucosyllactose and lacto-N-neotetraose, 2'-fucosyllactose and 3'-sialyllactose, 2'-fucosyllactose and 6'-sialyllactose, difucosyllactose and 3-fucosyllactose, difucosyllactose and lacto-N-tetraose, difucosyllactose and lacto-N-neotetraose, difucosyllactose and 3'-sialyllactose, difucosyllactose and 6'-sialyllactose, 3-fucosyllactose and lacto-N-tetraose, 3-fucosyllactose and lacto-N-neotetraose, 3-fucosyllactose and 3'-sialyllactose, 3-fucosyllactose and 6'-sialyllactose, lacto-N-tetraose and lacto-N-neotetraose, lacto-N-tetraose and 3'-sialyllactose, lacto-N-tetraose and 6'-sialyllactose, lacto-N-neotetraose and 3'-sialyllactose, lacto-N-neotetraose and 6'-sialyllactose, or 3'-sialyllactose and 6'-sialyllactose.

In some embodiments, the fermentation composition includes at least three human milk oligosaccharides produced from the yeast cells. The at least three human milk oligosaccharides in the fermentation composition can include, for example, 2'-fucosyllactose, difucosyllactose, and 3-fucosyllactose; 2'-fucosyllactose, difucosyllactose, and lacto-N-tetraose; 2'-fucosyllactose, difucosyllactose, and lacto-N-neotetraose; 2'-fucosyllactose, difucosyllactose, and 3'-sialyllactose; 2'-fucosyllactose, difucosyllactose, and 6'-sialyllactose; 2'-fucosyllactose, 3-fucosyllactose, and lacto-N-tetraose; 2'-fucosyllactose, 3-fucosyllactose, and lacto-N-neotetraose; 2'-fucosyllactose, 3-fucosyllactose, and 3'-sialyllactose; 2'-fucosyllactose, 3-fucosyllactose, and 6'-sialyllactose; 2'-fucosyllactose, lacto-N-tetraose, and lacto-N-neotetraose; 2'-fucosyllactose, lacto-N-tetraose, and 3'-sialyllactose; 2'-fucosyllactose, lacto-N-tetraose, and 6'-sialyllactose; 2'-fucosyllactose, lacto-N-neotetraose, and 3'-sialyllactose; 2'-fucosyllactose, lacto-N-neotetraose, and 6'-sialyllactose; 2'-fucosyllactose, 3'-sialyllactose, and 6'-sialyllactose; difucosyllactose, 3-fucosyllactose, and lacto-N-tetraose; difucosyllactose, 3-fucosyllactose, and lacto-N-neotetraose; difucosyllactose, 3-fucosyllactose, and 3'-sialyllactose; difucosyllactose, 3-fucosyllactose, and 6'-sialyllactose; difucosyllactose, lacto-N-tetraose, and lacto-N-neotetraose; difucosyllactose, lacto-N-tetraose, and 3'-sialyllactose; difucosyllactose, lacto-N-tetraose, and 6'-sialyllactose; difucosyllactose, lacto-N-neotetraose, and 3'-sialyllactose; difucosyllactose, lacto-N-neotetraose, and 6'-sialyllactose; difucosyllactose, 3'-sialyllactose, and 6'-sialyllactose; 3-fucosyllactose, lacto-N-tetraose, and lacto-N-neotetraose; 3-fucosyllactose, lacto-N-tetraose, and 3'-sialyllactose; 3-fucosyllactose, lacto-N-tetraose, and 6'-sialyllactose; 3-fucosyllactose, lacto-N-neotetraose, and 3'-sialyllactose; 3-fucosyllactose, lacto-N-neotetraose, and 6'-sialyllactose; 3-fucosyllactose, 3'-sialyllactose, and 6'-sialyllactose; lacto-N-tetraose, lacto-N-neotetraose, and 3'-sialyllactose; lacto-N-tetraose, lacto-N-neotetraose, and 6'-sialyllactose; or lacto-N-neotetraose, 3'-sialyllactose, and 6'-sialyllactose. In some embodiments, the fermentation composition includes at least four human milk oligosaccharides produced from the yeast cells. In some embodiments, the fermentation composition includes at least five human milk oligosaccharides produced from the yeast cells. In some embodiments, the fermentation composition includes at least six human milk oligosaccharides produced from the yeast cells. In some embodiments, the fermentation composition includes at least seven human milk oligosaccharides produced from the yeast cells.

The mass fraction of difucosyllactose within the one or more produced human milk oligosaccharides can be, for example, between 0 and 50%, e.g., between 0 and 30%, between 5% and 35%, between 10% and 40%, between 15% and 45%, or between 20% and 40%. In terms of upper limits, the mass fraction of difucosyllactose in the human milk oligosaccharides can be less than 50%, e.g., less than 45%, less than 40%, less than 35%, less than 30%, less than 25%, less than 20%, less than 15%, less than 10%, or less than 5%.

VI. Methods of Recovering Human Milk Oligosaccharides

Also provided are methods of recovering one or more human milk oligosaccharides from a fermentation composition. In some embodiments, the fermentation composition is any of the fermentation composition disclosed herein and described above. The method includes separating at least a portion of a population of yeast cells from a culture medium. In some embodiments, the separating includes centrifugation. In some embodiments, the separating includes filtration.

While some portion of the one or more human milk oligosaccharides produced by the cells during fermentation can be expected to partition with the culture medium during the separation of the yeast cells from the medium, some of the human milk oligosaccharides can be expected to remain associated with the yeast cells. One approach to capturing this cell-associated product and improving overall recovery yields is to rinse the separated cells with a wash solution that is then collected. It has now been found that the effectiveness of such a rinse can be significantly increased by heating the wash solution prior to its use.

Accordingly, the provided recovery methods further include contacting the separated yeast cells with a heated wash liquid. In some embodiments, the heated wash liquid is a heated aqueous wash liquid. In some embodiments, the heated wash liquid consists of water. In some embodiments, the heated wash liquid includes one or more other liquid or dissolved solid components.

The temperature of the heated aqueous wash liquid can be, for example, between 30° C. and 90° C., e.g., between 30° C. and 66° C., between 36° C. and 72° C., between 42° C. and 78° C., between 48° C. and 84° C., or between 54° C. and 90° C. In terms of upper limits, the wash temperature can be less than 90° C., e.g., less than 84° C., less than 78° C., less than 72° C., less than 66° C., less than 60° C., less than 54° C., less than 48° C., less than 42° C., or less than 36° C.

In terms of lower limits, the wash temperature can be greater than 30° C., e.g., greater than 36° C., greater than 42° C., greater than 48° C., greater than 54° C., greater than 60° C., greater than 66° C., greater than 72° C., greater than 78° C., or greater than 84° C. Higher temperatures, e.g., greater than 90° C., and lower temperatures, e.g., less than 30° C., are also contemplated.

The method further includes, subsequent to the contacting of the separated yeast cells with the heated wash liquid, removing the wash liquid from the yeast cells. In some embodiments, the removed wash liquid is combined with the separated culture medium and further processed to isolate the produced one or more human milk oligosaccharides. In some embodiments, the removed wash liquid and the separated culture medium are further processed independently of one another. In some embodiments, the removal of the wash liquid from the yeast cells includes centrifugation. In some embodiments, the removal of the wash liquid from the yeast cells includes filtration.

The recovery yield can be such that, for at least one of the one or more human milk oligosaccharides produced from the yeast cells, the mass fraction of the produced at least one human milk oligosaccharide recovered in the combined culture medium and wash liquid is, for example, between 70% and 100%, e.g., between 70% and 88%, between 73% and 91%, between 76% and 94%, between 79% and 97%, or between 82% and 100%. In terms of lower limits, the recovery yield of at least one of the one or more human milk oligosaccharides can be greater than 70%, e.g., greater than 73%, greater than 76%, greater than 79%, greater than 82%, greater than 85%, greater than 88%, greater than 91%, greater than 94%, or greater than 97%. The recovery yield can be such that, for each of the one or more human milk oligosaccharides produced from the yeast cells, the mass fraction recovered in the combined culture medium and wash liquid is, for example, between 70% and 100%, e.g., between 70% and 88%, between 73% and 91%, between 76% and 94%, between 79% and 97%, or between 82% and 100%. In terms of lower limits, the recovery yield of each of the one or more human milk oligosaccharides can be greater than 70%, e.g., greater than 73%, greater than 76%, greater than 79%, greater than 82%, greater than 85%, greater than 88%, greater than 91%, greater than 94%, or greater than 97%.

While the compositions and methods provided herein have been described with respect to a limited number of embodiments, one or more features from any of the embodiments described herein or in the figures can be combined with one or more features of any other embodiment described herein in the figures without departing from the scope of the disclosure. No single embodiment is representative of all aspects of the methods or compositions. In certain embodiments, the methods can include numerous steps not mentioned herein. In certain embodiments, the methods do not include any steps not enumerated herein. Variations and modifications from the described embodiments exist.

All publications and patent applications mentioned in this specification are herein incorporated by reference to the same extent as if each individual publication or patent application was specifically and individually indicated to be incorporated by reference. Although the claimed subject matter has been described in some detail by way of illustration and example for purposes of clarity of understanding, it will be readily apparent to those of ordinary skill in the art in light of the teachings herein that certain changes and modifications may be made thereto without departing from the spirit or scope of the appended claims.

VII. Methods of Treating a Fermentation Composition

Also provided are methods of treating a fermentation composition. The treatment methods are particularly useful for increasing the yield of 2'-fucosyllactose within fermentation compositions that include difucosyllactose. In some embodiments, the fermentation composition is any of the fermentation composition disclosed herein and described above. The method includes providing a fermentation composition comprising difucosyllactose. The concentration of difucosyllactose in the fermentation composition can be as described above. The method further includes contacting the fermentation with an enzyme capable of converting difucosyllactose to 2'-fucosyllactose, e.g., an α1-3,4 fucosidase. The α1-3,4 fucosidase can be encoded by a gene engineered into a strain of the fermentation, such that the α1-3,4 fucosidase is expressed during the fermentation. The α1-3,4 fucosidase can be exogenously added to the fermentation composition as part of a downstream processing protocol. Suitable α1-3,4 fucosidase sources include, for example and without limitation, *Bacteroides thetaiotaomicron*, *Bifidobacterium bifidum*, *Bifidobacterium longum*, *Bifidobacterium longum* subsp. *infantis*, *Clostridium perfringens*, *Lactobacillus casei*, *Paenibacillus thiaminolyticus*, *Pseudomonas putida*, *Thermotoga maritima*, *Xanthomonas campestris* pv. *campestris*, *Arabidopsis thaliana*, and *Rattus norvegicus*.

The contacting of the fermentation composition with the α1-3,4 fucosidase is under conditions suitable for converting at least a portion of the difucosyllactose to 2'-fucosyllactose. The percentage of initial difucosyllactose converted by the α1-3,4 fucosidase can be, for example, between 20% and 100%, e.g., between 20% and 68%, between 28% and 76%, between 36% and 84%, between 44% and 92%, or between 52% and 100%. In terms of lower limits, the percent conversion of the difucosyllactose can be greater than 20%, e.g., greater than 28%, greater than 36%, greater than 44%, greater than 52%, greater than 60%, greater than 68%, greater than 76%, greater than 84%, or greater than 92%. In some embodiments, the fermentation composition further comprises 3-fucosyllactose, and the contacting of the fermentation composition with the α1-3,4 fucosidase also includes reducing the level of 3-fucosyllactose in the fermentation composition, further improving 2'-fucosyllactose purity in the composition.

VIII. Examples

The present disclosure will be better understood in view of the following non-limiting examples. The following examples are intended for illustrative purposes only and do not limit in any way the scope of the present invention.

Figure 4:
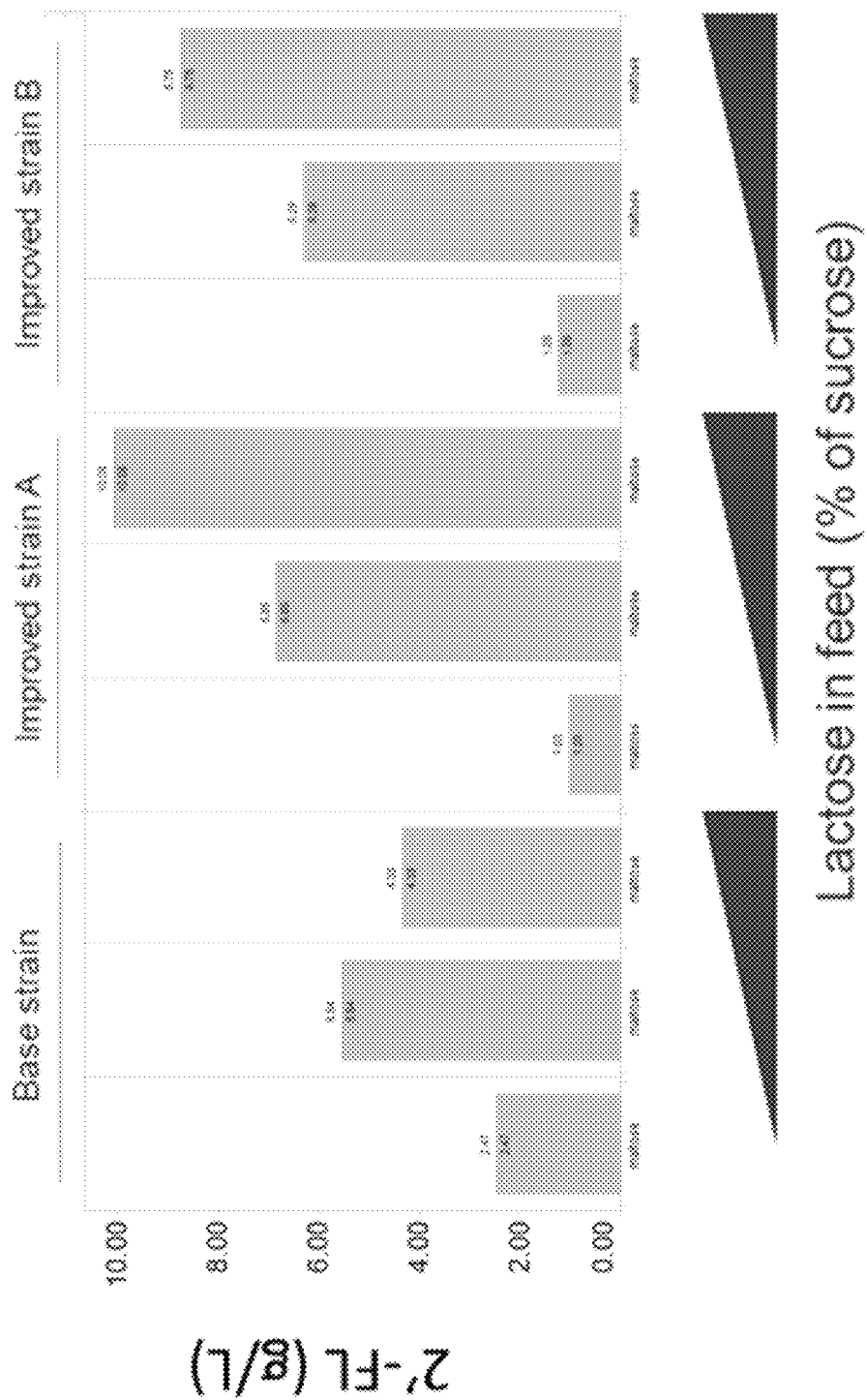
FIG. 4 presents graphs showing an increase in fed-batch fermentation production of 2'-fucosyllactose by genetically modified yeast cultured in media having increasing ratios of lactose to sucrose.

Example 1. Effect of Relative Sucrose and Lactose Medium Concentrations on Human Milk Oligosaccharide Production The influence of the sucrose to lactose ratio on human milk oligosaccharide production was explored in fermentor cultures of yeast genetically modified to produce 2'-fucosyllactose. The mass ratio of sucrose to lactose in the feed of these feb-batch fermentations ranged from 4 (i.e., 4:1) to 40 (i.e., 40:1). Results are shown in the graphs of FIG. 4. It can be seen from the data that increasing the fraction of lactose in the feed had a significant impact on total 2'-fucosyllactose production. Improved production strains especially benefited from the additional lactose, with 2'-fucosyllactose product concentrations increasing from less than 1.3 g/L to as much as 10 g/L.

Figure 5:
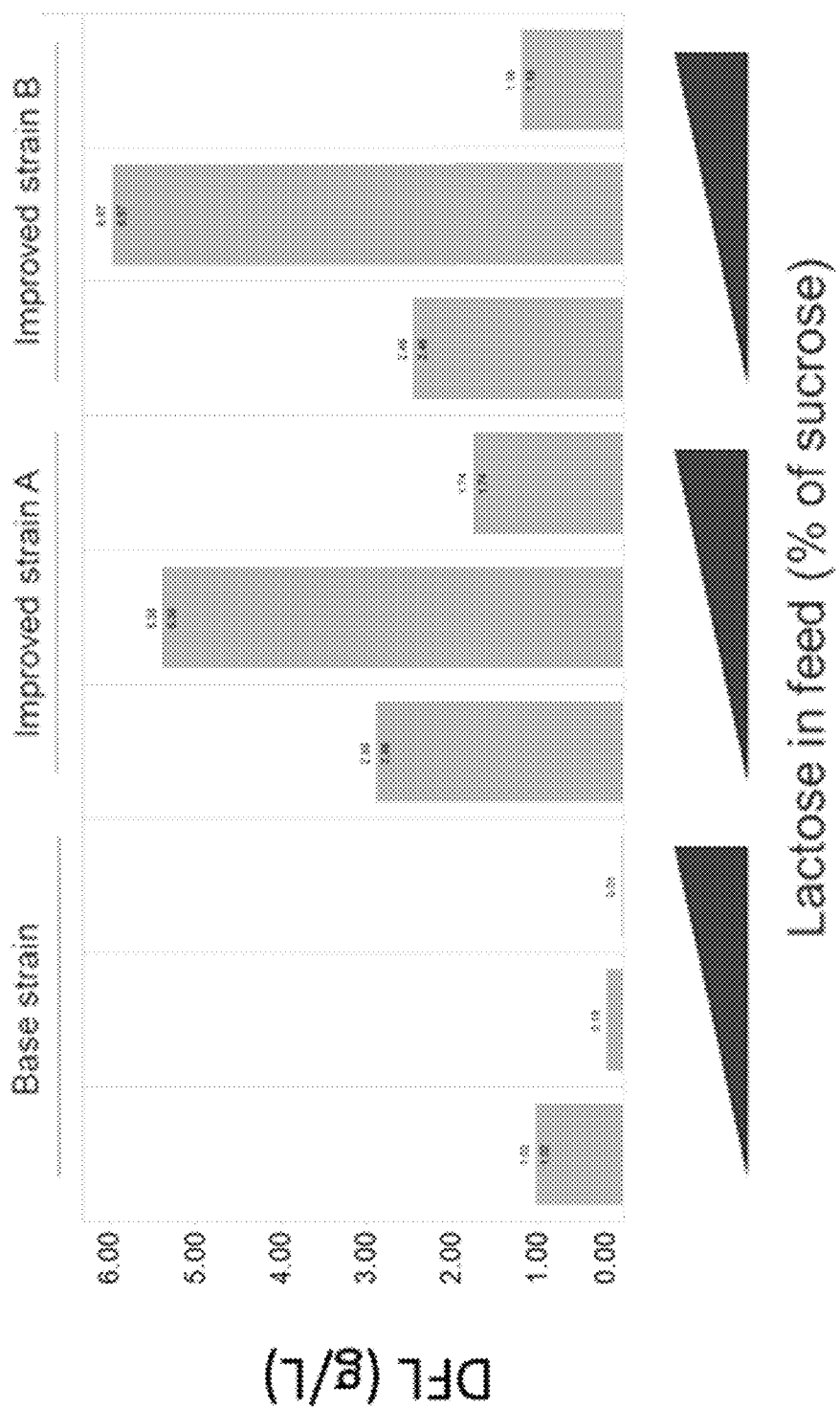
FIG. 5 presents graphs showing a decrease in fed-batch fermentation production of difucosyllactose by genetically modified yeast cultured in media having increasing ratios of lactose to sucrose.
Figure 6:
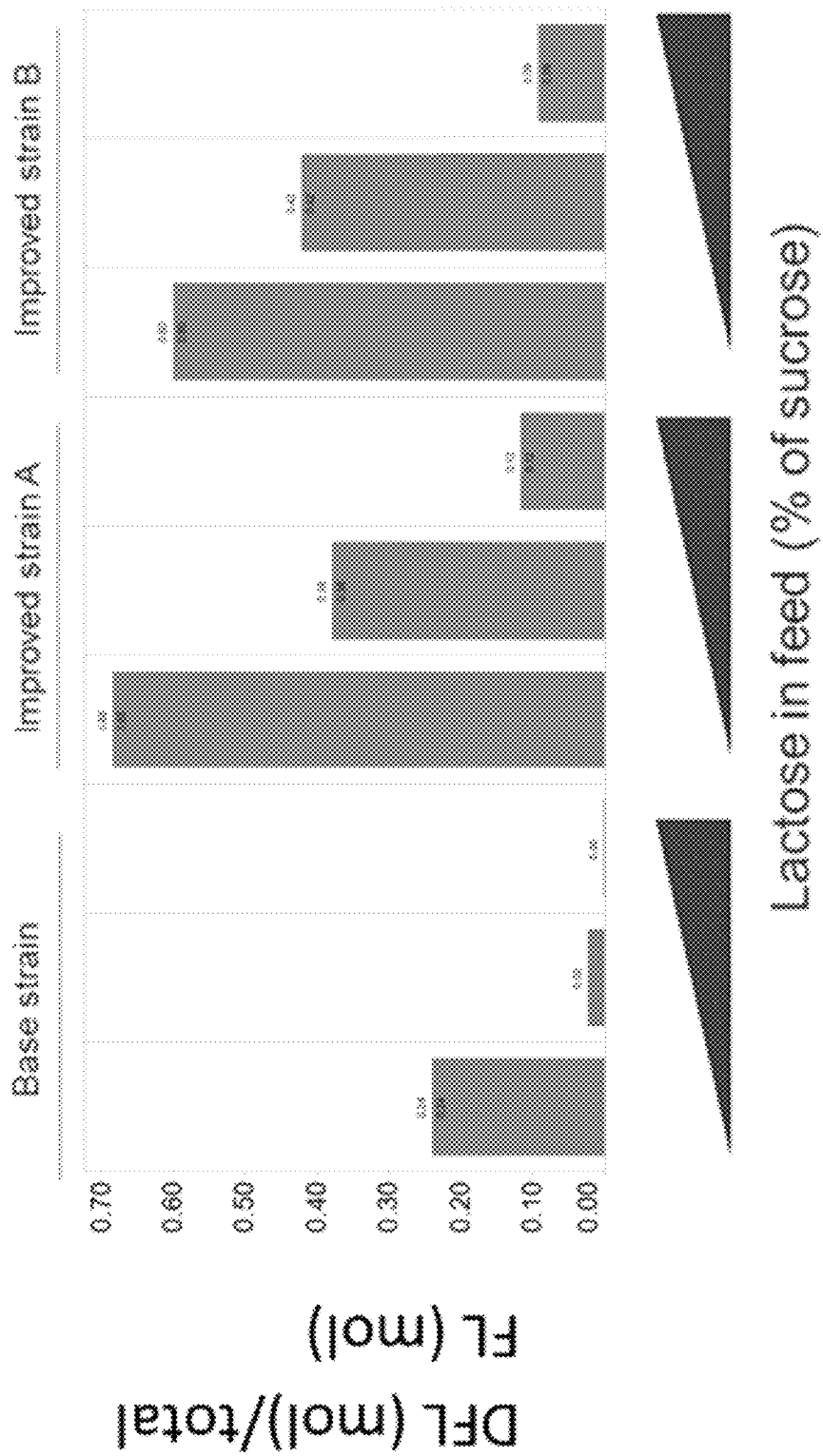
FIG. 6 presents graphs showing a decrease in fed-batch fermentation difucosyllactose production as a fraction of total fucosyllated products by genetically modified yeast cultured in media having increasing ratios of lactose to sucrose.

In addition, the increase in the lactose feed relative to the sucrose feed was also observed to alter the human milk oligosaccharide product profile of the yeast cells in the microfermentors by decreasing difucosyllactose production. From the data in the graphs of FIG. 5, it can be seen that for all three strains the lowest difucosyllactose product concentration was observed for the case of the highest lactose feed concentration. Furthermore, the data in the graphs of FIG. 6 indicated that as lactose increases as a fraction of the feed, the molar ratio of difucosyllactose to total fucosyllactoses, i.e., difucosyllactose together with 2'-fucosyllactose, decreases. These findings suggest that the ratio of sucrose to lactose can be varied to alter the specificity of a fucosyltransferase. Importantly, the results also show that it is possible to alter the product profile of human milk oligosaccharides generated by the genetically modified yeast cells disclosed herein without further altering their genetic makeup. As discussed above, this additional control strategy has significant implications for increasing desired product titers, decreasing undesired side product formation, and simplifying downstream recovery processes.

Figure 7:
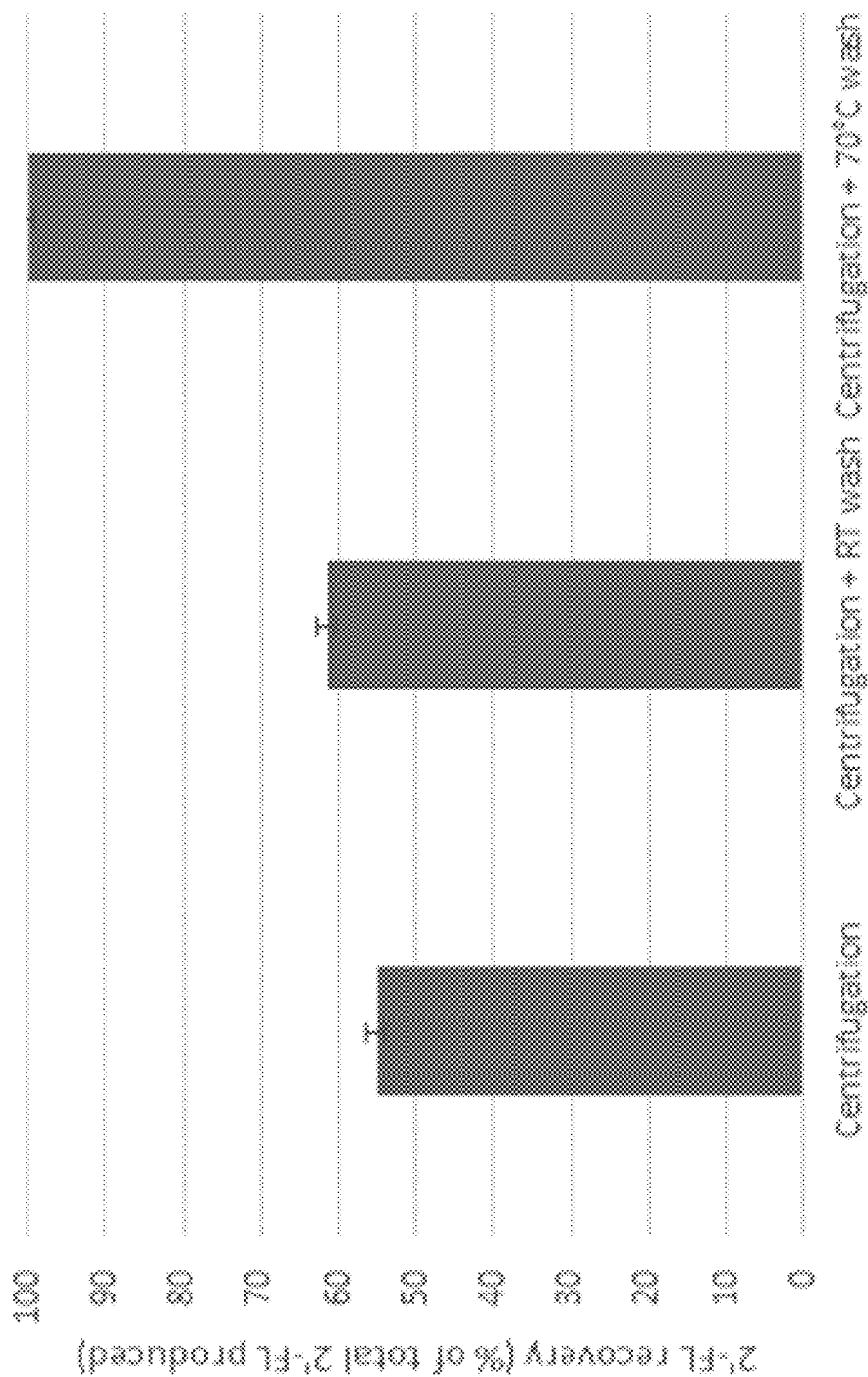
FIG. 7 presents a graph of increasing 2'-fucosyllactose recovery by washing cultured yeast with a heated aqueous wash liquid.
Figure 8:
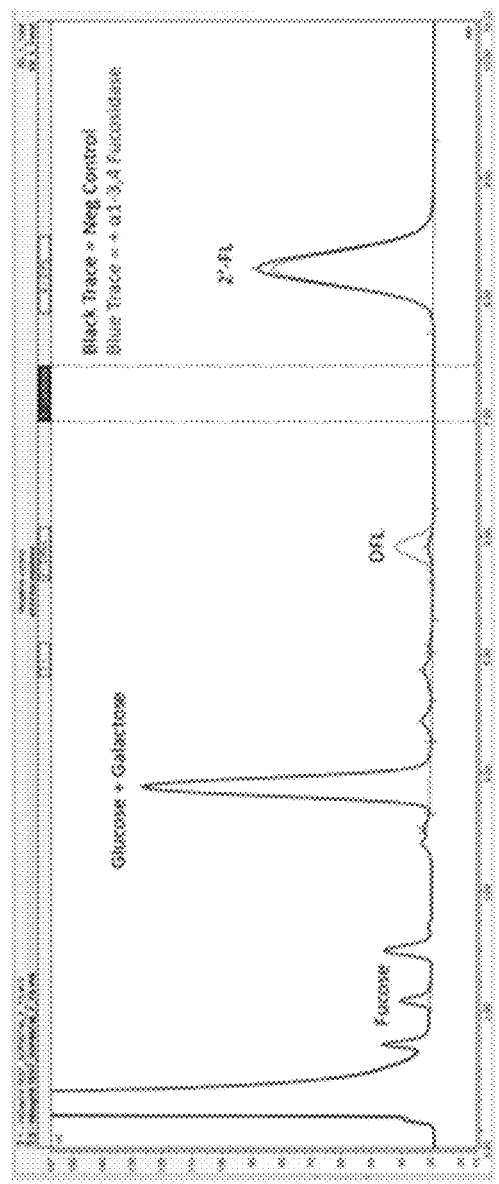
FIG. 8 presents a graph of increasing yield of 2'-fucosyllactose within a fermentation composition by treating the composition with a fucosidase.
Figure 9:
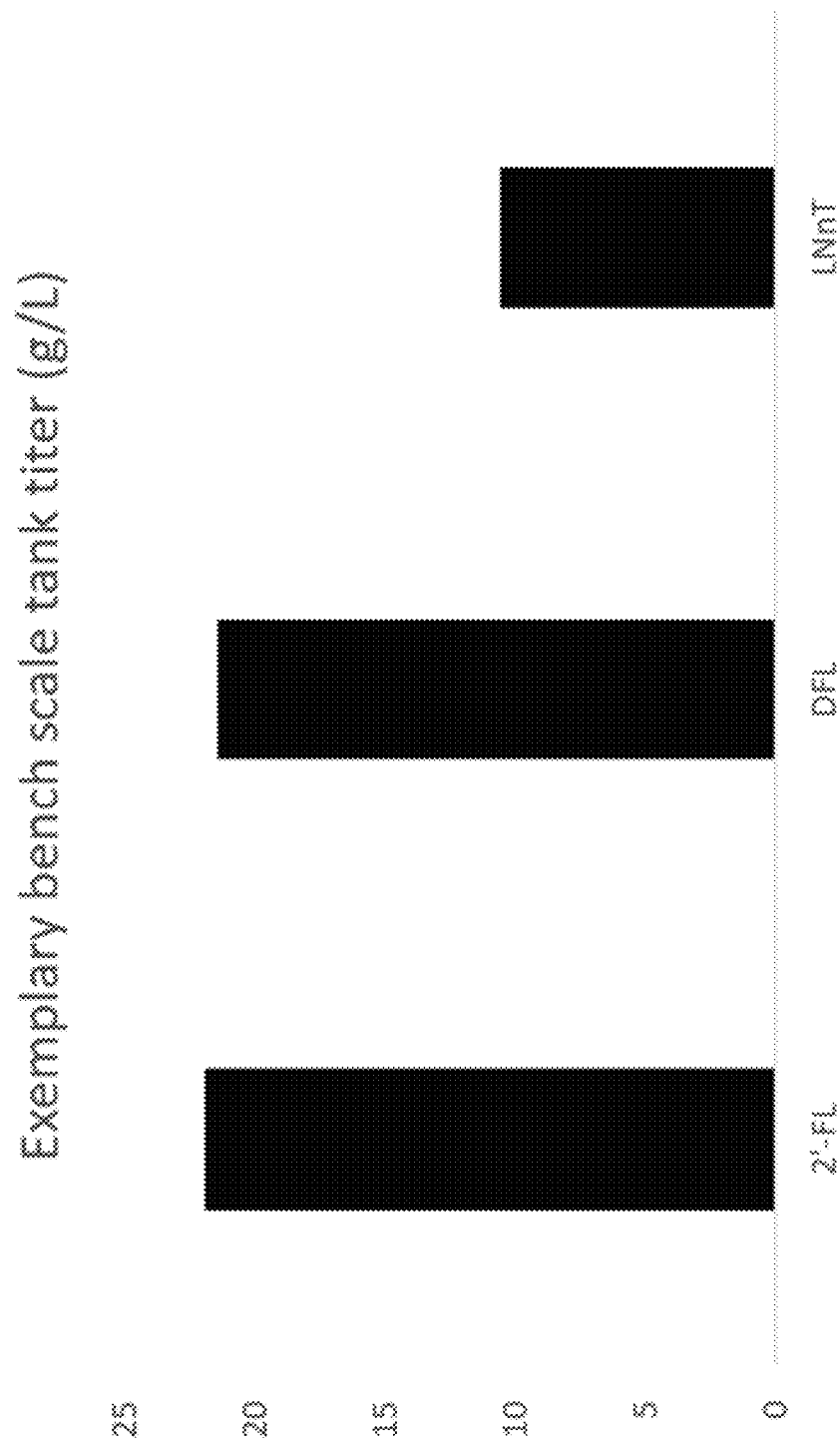
FIG. 9 presents a graph of exemplary concentrations of 2'-fucosyllactose (2'-FL), difucosyllactose (DFL), and lacto-N-neotetraose (LNnT) produced using the methods and compositions disclosed herein.

Example 2. Recovery of Human Milk Oligosaccharides from Fermentation Compositions Another experiment was performed to study the effects of different product isolation approaches for recovering human milk oligosaccharides produced with the provided yeast cells and fermentation methods. A sample of a fermentation culture including genetically modifies yeast cells and 2'-fucosyllactose generated from the cells was centrifuged, and the amount of 2'-fucosyllactose in the centrifugation supernatant was determined. As shown in the graph of FIG. 7, this standard centrifugation, which separates the aqueous fermentation broth from the yeast biomass, resulted in a recovery of approximately half of the produced 2'-fucosyllactose present in the original fermentation culture sample. In other words, approximately half of the 2'-fucosyllactose was associated with the yeast biomass, either extracellularly or intracellularly. It was found that washing the yeast with room temperature (RT) water minimally improves recovery. However, washing with 70° C. water substantially improved recovery to almost 100%. This finding demonstrates the advantages of the provided method of recovering human milk oligosaccharides from a fermentation composition by contacting the yeast cells of the composition with a heated aqueous wash liquid.

What is claimed is:

1. A genetically modified yeast cell capable of producing one or more human milk oligosaccharides, the yeast cell comprising one or more heterologous nucleic acids, each nucleic acid independently encoding at least one enzyme of a human milk oligosaccharide biosynthetic pathway, wherein the yeast cell does not comprise a heterologous nucleic acid encoding a fucokinase, and wherein the one or more heterologous nucleic acids are integrated into the genome of the yeast cell.

2. The genetically modified yeast cell of claim 1, wherein the one or more human milk oligosaccharides are selected from the group consisting of 2'-fucosyllactose, 3-fucosyllactose, lacto-N-tetraose, lacto-N-neotetraose, 3'-siallyllactose, 6'-siallyllactose, and difucosyllactose; and wherein the one or more heterologous nucleic acids each independently encode at least one enzyme selected from the group consisting of a GDP-mannose 4,6-dehydratase, a GDP-L-fucose synthase, an α-1,2-fucosyltransferase, an α-1,3-fucosyltransferase, a fucosidase, a β-1,3-N-acetylglucosaminyltransferase, a β-1,3-galactosyltransferase, a β-1,4-galactosyltransferase, a UDP-N-acetylglucosamine diphosphorylase, a CMP-Neu5Ac synthetase, a sialic acid synthase, a UDP-N-acetylglucosamine 2-epimerase, a UDP-N-acetylglucosamine diphosphorylase, a CMP-N-acetylneuraminate-β-galactosamide-α-2,3-sialyltransferase, and a β-galactoside-α-2,6-sialyltransferase.

3. The genetically modified yeast cell of claim 1, wherein the one or more human milk oligosaccharides are selected from the group consisting of 2'-fucosyllactose, 3-fucosyllactose, lacto-N-tetraose, and difucosyllactose; and wherein the one or more heterologous nucleic acids each independently encode at least one enzyme selected from the group consisting of a GDP-mannose 4,6-dehydratase, a GDP-L-fucose synthase, an α-1,2-fucosyltransferase, an α-1,3-fucosyltransferase, a fucosidase, a β-1,3-N-acetylglucosaminyltransferase, a β-1,4-galactosyltransferase, and a UDP-N-acetylglucosamine diphosphorylase.

4. The genetically modified yeast cell of claim 1, wherein the one or more human milk oligosaccharides comprise 2'-fucosyllactose, and wherein the enzymes encoded by the one or more heterologous nucleic acids comprise one or more of a GDP-mannose 4,6-dehydratase, a GDP-L-fucose synthase, an α-1,2-fucosyltransferase, and a fucosidase.

5. The genetically modified yeast cell of claim 1, wherein the one or more human milk oligosaccharides comprise 3-fucosyllactose, and wherein the enzymes encoded by the one or more heterologous nucleic acids comprise one or more of a GDP-mannose 4,6-dehydratase, a GDP-L-fucose synthase, an α-1,3-fucosyltransferase, and a fucosidase.

6. The genetically modified yeast cell of claim 1, wherein the one or more human milk oligosaccharides comprise lacto-N-tetraose, and wherein the enzymes encoded by the one or more heterologous nucleic acids comprise one or more of a β-1,3-N-acetylglucosaminyltransferase, a β-1,3-galactosyltransferase, and a UDP-N-acetylglucosamine diphosphorylase.

7. The genetically modified yeast cell of claim 1, wherein the one or more human milk oligosaccharides comprise lacto-N-neotetraose, and wherein the enzymes encoded by the one or more heterologous nucleic acids comprise one or more of a β-1,3-N-acetylglucosaminyltransferase, a β-1,4-galactosyltransferase, and a UDP-N-acetylglucosamine diphosphorylase.

8. The genetically modified yeast cell of claim 1, wherein the one or more human milk oligosaccharides comprise 3'-sialyllactose, and wherein the enzymes encoded by the one or more heterologous nucleic acids comprise one or more of a CMP-Neu5Ac synthetase, a sialic acid synthase, a UDP-N-acetylglucosamine 2-epimerase, a UDP-N-acetylglucosamine diphosphorylase, and a CMP-N-acetylneuraminate-β-galactosamide-α-2,3-sialyltransferase.

9. The genetically modified yeast cell of claim 1, wherein the one or more human milk oligosaccharides comprise 6'-sialyllactose, and wherein the enzymes encoded by the one or more heterologous nucleic acids comprise one or more of a CMP-Neu5Ac synthetase, a sialic acid synthase, a UDP-N-acetylglucosamine 2-epimerase, a UDP-N-acetylglucosamine diphosphorylase, and a β-galactoside-α-2,6-sialyltransferase.

10. The genetically modified yeast cell of claim 1, wherein the one or more human milk oligosaccharides comprise difucosyllactose, and wherein the enzymes encoded by the one or more heterologous nucleic acids comprise one or more of a GDP-mannose 4,6-dehydratase, a GDP-L-fucose synthase, an α-1,2-fucosyltransferase, and an α-1,3-fucosyltransferase.

11. The genetically modified yeast cell of claim 1, wherein the yeast cell is *Saccharomyces cerevisiae*, and wherein the enzymes encoded by the one or more heterologous nucleic acids further comprise a lactose permease.

12. The genetically modified yeast cell of claim 1, wherein the yeast cell is *Kluyveromyces marxianus*, wherein the yeast cell further comprises a deletion of at least a portion of a nucleic acid encoding β-galactosidase.

13. The genetically modified yeast cell of claim 1, wherein expression of at least one of the one or more heterologous nucleic acids is regulated by the activity of a promoter that is responsive to a small molecule.

14. The genetically modified yeast cell of claim 13, wherein the small molecule is maltose or lysine.

15. A method of producing one or more human milk oligosaccharides, the method comprising:
providing a population of genetically modified yeast cells capable of producing one or more human milk oligosaccharides, each yeast cell comprising one or more heterologous nucleic acids, each nucleic acid independently encoding at least one enzyme of a human milk oligosaccharide biosynthetic pathway, wherein the one or more heterologous nucleic acids are integrated into the genome of the yeast cell;
feeding to the population a culture medium comprising sucrose and lactose, wherein the mass ratio of the sucrose to the lactose is less than 40; and
culturing the yeast cells in the culture medium under conditions suitable for the yeast cells to produce the one or more human milk oligosaccharides.

16. The method of claim 15, further comprising:
prior to the culturing, growing the population of genetically modified yeast cells in a growth medium comprising a small molecule, wherein expression of at least one of the one or more nucleic acids is positively regulated by the activity of a promoter responsive to the small molecule, wherein the concentration of the small molecule in the growth medium is sufficient to repress the promoter, and wherein the concentration of the small molecule in the culture medium during the culturing is sufficiently low that the promoter is activated.

17. The method of claim 16, wherein the small molecule is maltose or lysine.

18. The method of claim 15, wherein the genetically modified yeast cells do not comprise a heterologous nucleic acid encoding a fucokinase.

19. The method of claim 15, wherein the one or more human milk oligosaccharides are selected from the group consisting of 2'-fucosyllactose, 3-fucosyllactose, lacto-N-tetraose, and difucosyllactose; and wherein the one or more heterologous nucleic acids each independently encode at least one enzyme selected from the group consisting of a GDP-mannose 4,6-dehydratase, a GDP-L-fucose synthase, an α-1,2-fucosyltransferase, an α-1,3-fucosyltransferase, a fucosidase, a β-1,3-N-acetylglucosaminyltransferase, a β-1,4-galactosyltransferase, and a UDP-N-acetylglucosamine diphosphorylase.

20. The method of claim 15, wherein the one or more human milk oligosaccharides comprise 2'-fucosyllactose, and wherein the 2'-fucosyllactose is produced at a yield greater than 0.01 g/g sucrose.

21. The method of claim 15, wherein the one or more human milk oligosaccharides comprise 2'-fucosyllactose, and wherein the concentration of the 2'-fucosyllactose in the culture medium is greater than 5 g/l.

22. The method of claim 15, wherein the one or more human milk oligosaccharides comprise difucosyllactose, and wherein the concentration of the difucosyllactose in the culture medium is greater than 5 g/l.

23. The method of claim 15, wherein the one or more human milk oligosaccharides comprise 2'-fucosyllactose, and wherein the yeast cells produce less than 1 g difucosyllactose per g of the produced 2'-fucosyllactose.

24. The method of claim 15, wherein the one or more human milk oligosaccharides comprise lacto-N-neotetraose, and wherein the concentration of the lacto-N-neotetraose in the culture medium is greater than 0.5 g/l.

25. The method of claim 15, wherein the culture medium does not comprise fucose.

26. The method of claim 15, further comprising:
adjusting the mass ratio of the sucrose to the lactose, thereby altering the production of at least one of the one or more human milk oligosaccharides.

27. A method of treating a fermentation composition, the method comprising:
providing a fermentation composition comprising difucosyllactose; and
contacting the fermentation composition with α1-3,4 fucosidase under conditions suitable for catalyzing the conversion of at least a portion of the difucosyllactose to 2'-fucosyllactose with the α1-3,4 fucosidase;
wherein the fermentation composition comprises a population of genetically modified yeast cells capable of producing one or more human milk oligosaccharides, each yeast cell comprising one or more heterologous nucleic acids, each nucleic acid independently encoding at least one enzyme of a human milk oligosaccharide biosynthetic pathway, and wherein the genetically modified yeast cells do not comprise a heterologous nucleic acid encoding a fucokinase.

28. The method of claim 27, wherein the one or more human milk oligosaccharides are selected from the group consisting of 2'-fucosyllactose, 3-fucosyllactose, lacto-N-tetraose, and difucosyllactose; and wherein the one or more heterologous nucleic acids each independently encode at least one enzyme selected from the group consisting of a GDP-mannose 4,6-dehydratase, a GDP-L-fucose synthase, an α-1,2-fucosyltransferase, an α-1,3-fucosyltransferase, a fucosidase, a β-1,3-N-acetylglucosaminyltransferase, a β-1,4-galactosyltransferase, and a UDP-N-acetylglucosamine diphosphorylase.

* * * * *